(12) United States Patent
Coffman et al.

(10) Patent No.: US 6,464,942 B2
(45) Date of Patent: Oct. 15, 2002

(54) PLATE ALIGNMENT AND SAMPLE TRANSFER INDICIA FOR A MULTIWELL MULTIPLATE STACK AND METHOD FOR PROCESSING BIOLOGICAL/CHEMICAL SAMPLES USING THE SAME

(75) Inventors: Jonathan L. Coffman, Princeton, MA (US); Hong Lu, Shrewsbury, MA (US); Ernest J. Woods, III, Upton, MA (US)

(73) Assignee: Ciphergen Biosystems, Inc., Fremont, CA (US)

(*) Notice: Subject to any disclaimer, the term of this patent is extended or adjusted under 35 U.S.C. 154(b) by 0 days.

(21) Appl. No.: 09/316,850

(22) Filed: May 21, 1999

(65) Prior Publication Data

US 2001/0001644 A1 May 24, 2001

Related U.S. Application Data

(63) Continuation of application No. 09/035,422, filed on Mar. 5, 1998, now abandoned, which is a continuation-in-part of application No. 08/948,915, filed on Oct. 10, 1997, now abandoned.

(51) Int. Cl.$^7$ .................................................. B01L 3/00
(52) U.S. Cl. ....................... 422/100; 422/101; 422/102; 435/288.4; 435/305.1; 436/180
(58) Field of Search ................................ 422/100, 102, 422/942, 101, 944, 946, 947, 948; 435/288.4, 305.1; 436/180

(56) References Cited

U.S. PATENT DOCUMENTS

| | | | | |
|---|---|---|---|---|
| 4,493,815 A | * | 1/1985 | Fernwood et al. | 422/101 |
| 4,526,690 A | * | 7/1985 | Klovsky et al. | 210/335 |
| 4,772,487 A | | 9/1988 | Gotoh et al. | 427/2 |
| 4,902,481 A | * | 2/1990 | Clark et al. | 422/101 |
| 4,948,442 A | | 8/1990 | Manns | 156/73.1 |
| 4,948,564 A | * | 8/1990 | Root et al. | 422/101 |
| 5,047,215 A | | 9/1991 | Manns | 422/101 |
| 5,137,698 A | | 8/1992 | Ansorge et al. | 422/242 |
| 5,227,137 A | * | 7/1993 | Monti et al. | 422/101 |
| 5,262,128 A | * | 11/1993 | Leighton et al. | 422/100 |
| 5,283,039 A | * | 2/1994 | Aysta | 422/104 |
| 5,603,899 A | * | 2/1997 | Franskovich et al. | 422/100 |
| 5,620,663 A | | 4/1997 | Aysta et al. | 422/104 |
| 5,741,463 A | * | 4/1998 | Sanadi | 422/101 |
| 5,746,975 A | * | 5/1998 | Chateau | 422/61 |
| 5,846,493 A | * | 12/1998 | Bankier et al. | 422/101 |
| 5,958,714 A | * | 9/1999 | Gordon et al. | 210/238 |
| 5,961,925 A | * | 10/1999 | Ruediger et al. | 422/99 |
| 5,981,736 A | * | 11/1999 | Coffman | 536/25.4 |
| 6,083,761 A | * | 7/2000 | Kedar et al. | 436/178 |

FOREIGN PATENT DOCUMENTS

| | | |
|---|---|---|
| WO | WO 91/02073 | 2/1991 |
| WO | WO 93/19199 | 9/1993 |
| WO | WO 95/27196 | 10/1995 |
| WO | WO 97/15394 | 5/1997 |

* cited by examiner

*Primary Examiner*—Jill Warden
*Assistant Examiner*—Kathryn Bex
(74) *Attorney, Agent, or Firm*—Foley & Lardner

(57) ABSTRACT

Device and method for processing biological, biochemical or chemical samples are provided wherein a first multiwell plate is stacked atop a second multiwell plate. The first multiwell plate has x wells arranged in a regular array, each capable of receiving a separate sample. Each well of the x wells has an outlet at a lower surface of the first plate. The second multiwell plate has y wells arranged in a regular array, each well of the y wells being capable of receiving a separate sample, and wherein y>x. The outlets at the lower surface of the first multiwell plate are arrayed to register with corresponding inlets of a subset of the y wells of the second multiwell plate when the first plate is stacked atop the second plate. A mechanism for aligning the first plate to the second plate is provided, as well as transfer indicia for tracking transfer of sample from the first plate to the second plate. Also, a mechanism for sealing the first plate to the second plate is provided so that samples can be directly transferred between the first plate and the second plate without cross-contamination occurring in open wells of the second plate.

23 Claims, 19 Drawing Sheets

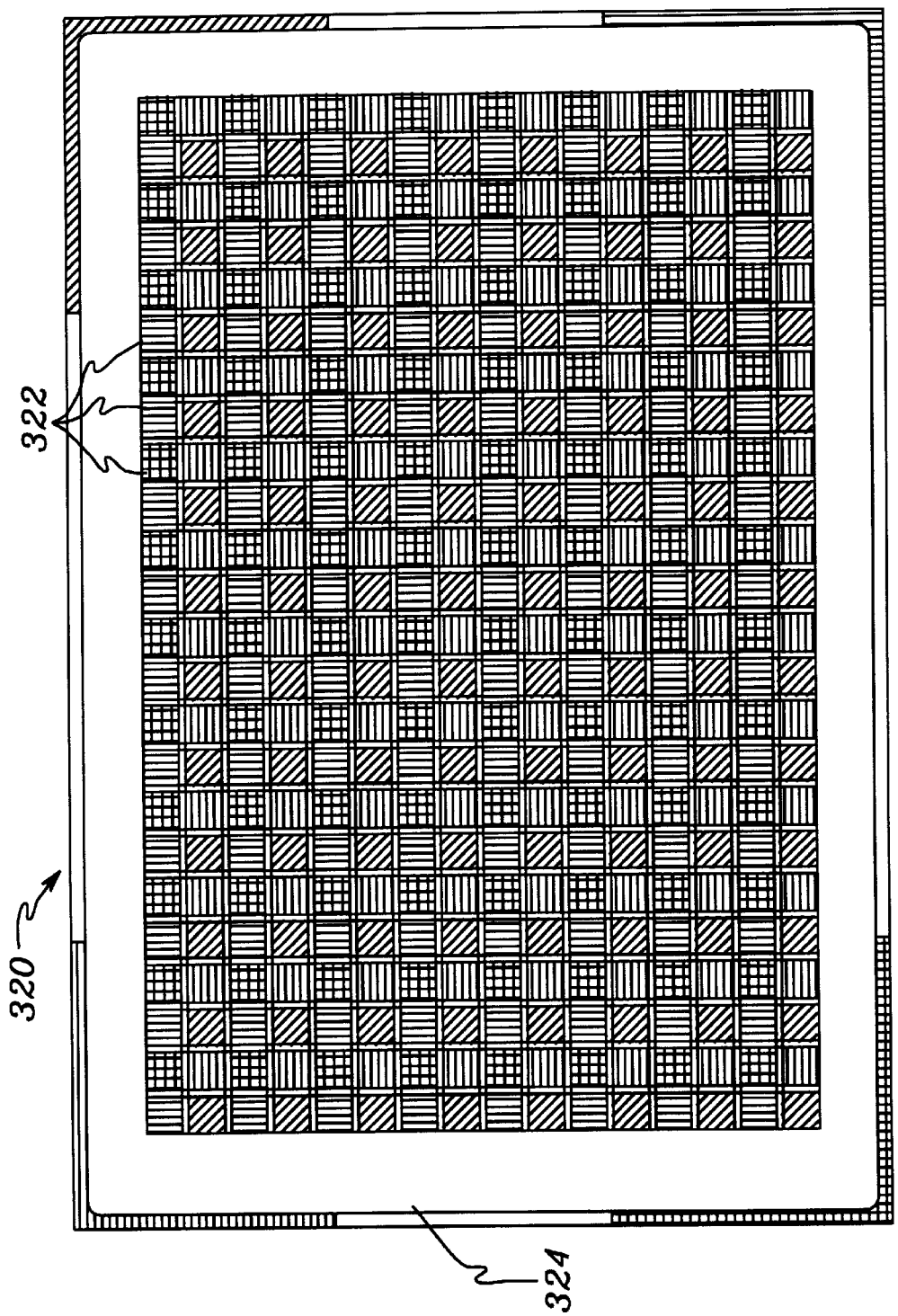

PLATE ALIGNMENT AND SAMPLE TRANSFER INDICIA FOR A MULTIWELL MULTIPLATE STACK AND METHOD FOR PROCESSING BIOLOGICAL/CHEMICAL SAMPLES USING THE SAME

CROSS-REFERENCE TO RELATED APPLICATION

This application is a continuation of patent application Ser. No. 09/035,422 filed Mar. 5, 1998, now abandoned, which is a continuation-in-part patent application from commonly assigned, U.S. patent application by Coffman et al. entitled "Multiwell Multiplate Stack and Method For Processing Biological/Chemical Samples Using the Same," Ser. No. 08/948,915 filed Oct. 10, 1997 now abandoned, the entirety of which is hereby incorporated herein by reference.

TECHNICAL FIELD

This invention relates in general to biological, biochemical and chemical assays, and more particularly, to a sampling and filtration device comprising a stack of multiwell plates which is useful in processing such assays.

BACKGROUND OF THE INVENTION

Multiwell test plates used for isotopic and non-isotopic in-vitro assays are well known in the art and are exemplified, for example, by those described in U.S. Pat. Nos. 3,111,489; 3,540,856; 3,540,857; 3,540,858; 4,304,865; 4,948,442; and 5,047,215. Typically, such test plates have been standardized in the form of the so-called micro-titre plate that provides, in one example, 96 depressions or cylindrical wells of about 0.66 cm in diameter and 1.3 cm deep, arranged in a 12×8 regular rectangular array spaced about 0.9 cm center-to-center.

Selected wells in such a test-plate are used to incubate respective microcultures, followed by further processing to harvest the incubated material. Each well typically includes a filtration element so that, upon application of a vacuum to one side of the plate, fluid in each well is expressed through the filter leaving solids, such as bacteria, debris and the like, entrapped in the well. In typical use, specimens from up to 96 different individuals may be respectively inserted in corresponding wells in the multiwell plate in the course of an assay, the specimens typically all being inserted prior to filtration and completion of the assay.

Oftentimes, it is necessary to transfer biological/chemical samples from one multiwell test plate to another multiwell test plate. The conventional approach to transferring samples is to pipette the samples from the first test plate to the second test plate. However, this approach can be time consuming and difficult depending upon the plate configurations between which samples are being transferred. For example, micro-titre plates providing 384 or 864 cylindrical wells arranged in a regular rectangular array have recently become available. Since each well of a 96-well plate can hold 400 $\mu$l or more of sample, while a well of a 384-well plate can only hold, for example, 100 $\mu$l of sample, it is conventionally necessary to pipette sample from each well of the 96-well plate to four different wells of the 384-well plate. Obviously, this procedure can be tedious.

With the availability of the new multiwell plates, various assay processing enhancements are desirable. In particular, enhancements in the transfer process are needed for moving samples from, for example, a 96-well plate to a 384- or 864-well plate. The present invention is directed to providing these processing enhancements for the transfer of samples between different multiwell plates.

DISCLOSURE OF THE INVENTION

Briefly summarized, this invention comprises in a first aspect a device for processing biological, biochemical or chemical samples comprising a first multiwell plate and a second multiwell plate. The first multiwell plate has x wells arranged in a regular array, each well of the x wells being capable of receiving a separate sample, and wherein each well of the x wells has an outlet at a lower surface of the first multiwell plate. The second multiwell plate has y wells arranged in a regular array, each well of the y wells being capable of receiving a separate sample, and wherein y≧x. The outlets at the lower surface of the first multiwell plate are arrayed to register with corresponding inlets of x' wells of the y wells of the second multiwell plate when the first multiwell plate is stacked atop the second multiwell plate, wherein x=x. A means for aligning the first multiwell plate to the second multiwell plate is also provided so that the x wells of the first multiwell plate automatically align to the x' wells of the second multiwell plate when the first multiwell plate is stacked atop the second multiwell plate using the alignment means. Samples can be directly transferred from the x wells of the first multiwell plate to the x' wells of the second multiwell plate. As an enhanced aspect, the means for aligning may comprise alignment indicia disposed on the first multiwell plate and corresponding alignment indicia on the second multiwell plate, and/or an alignment guide coupled to either the first multiwell plate or the second multiwell plate so that the x wells of the first multiwell plate automatically align to the x' wells of the second multiwell plate when the plates are stacked using the alignment indicia and/or guide.

In another aspect, the invention comprises a device for processing biological/chemical samples which includes a first multiwell plate and a second multiwell plate. The first multiwell plate has x wells arranged in a regular array, each well of the x wells being capable of receiving a separate sample, and the second multiwell plate has y wells arranged in a regular array, each well of the y wells also being capable of receiving a separate sample. The device further includes transfer indicia for tracking transfer of sample from the first multiwell plate to the second multiwell plate. The transfer indicia, initially disposed within the x wells of the first multiwell plate, may comprise an inert color indicia which automatically transfers to the second multiwell plate upon transfer of samples from the x wells of said first multiwell plate to wells of said second multiwell plate.

In another aspect, the invention comprises a method for processing biological, biochemical or chemical samples comprising: providing a first multiwell plate having x wells arranged in a regular array, each well of the x wells being capable of receiving a separate sample; providing a second multiwell plate having y wells arranged in a regular array, each well of the y wells being capable of receiving a separate sample; providing transfer indicia within at least one well having sample therein of the x wells of the first multiwell plate; and transferring sample from the first multiwell plate to the second multiwell plate, the transferring including transferring the transfer indicia from the at least one well of the first multiwell plate to at least one well of the second multiwell plate, wherein the transfer indicia tracks transfer of sample from the at least one well of the first multiwell plate to the at least one well of the second multiwell plate for monitoring possible cross-contamination of wells of the second multiwell plate.

To restate, various techniques are provided herein for directly transferring samples from a first well plate having a first number of wells to a second well plate having a second number of wells, wherein the second number of wells is equal to or greater than the first number of wells. Preferably, the second number of wells is a multiple of the first number of wells. As a specific example discussed herein, the first well plate may comprise a 96-well plate and the second well plate a 384-well plate. Significant time and processing complexity is saved by being able to directly transfer between two different multiwell plates. For example, pipetting apparatus is unnecessary to accomplish the transfer.

In addition to direct transfer of samples between well plates, a technique is provided herein to prevent cross-contamination between wells of the receiving plate, as well as to prevent drying of open wells within the receiving plate. In accordance with the principles of this invention, the first well plate may comprise a filter plate so that simultaneous transfer and filtering of samples occurs during the movement of samples from the first well plate to the second well plate. Further, the second well plate can comprise a chromatographic media so that purification of the sample can also simultaneously occur with transfer of the sample from the first well plate into (and through) the second well plate. In accordance with the principles of this invention, a greater volume of sample in the first well plate than can be accommodated in the second well plate can be simultaneously filtered in the first well plate, transferred from the first well plate to the second well plate and purified in the second well plate, before being discharged. Various further advantages, enhancements and examples of processings in accordance with this invention are described further herein.

For example, an alignment mechanism comprising alignment indicia and/or an alignment guide can be provided on either or both of the first multiwell plate and the second multiwell plate. The alignment indicia may comprise positional indicia such as matching color indicia at appropriate corners of the first multiwell plate and the second multiwell plate to facilitate alignment of the outlets of the first multiwell plate to a desired subset of wells of the second multiwell plate. Alternatively, the entire first multiwell plate could be color coded to match color coding on the second multiwell plate to facilitate alignment of the outlets of the first multiwell plate to the desired subset of wells of the second multiwell plate.

Advantageously, the invention also contemplates the use of inert transfer indicia, such as inert color indicia, within the wells for tracking transfer of sample from the wells of the first multiwell plate to the wells of the second multiwell plate. This transfer indicia can confirm proper transfer of samples from the x wells of the first multiwell plate to corresponding wells of the second multiwell plate, as well as indicate whether cross-contamination of samples has occurred between wells of the second multiwell plate. For example, different 96-well plates may have different colored transfer indicia which should be transferred with the samples thereof into a corresponding subset of wells of a 384 well plate. Cross-contamination is thus visually identifiable by verifying accuracy of the colors within the wells of the 384 well plate.

BRIEF DESCRIPTION OF THE DRAWINGS

The above-described objects, advantages and features of the present invention, as well as others, will be more readily understood from the following detailed description of certain preferred embodiments of the invention, when considered in conjunction with the accompanying drawings in which:

FIG. 18b is an isometric view of the 96-well plate 100a of FIG. 18a;

FIG. 19b is an isometric view of the 96-well plate 100b of FIG. 19a;

FIG. 20b is an isometric view of the 96-well plate 100c of FIG. 20a;

FIG. 21b is an isometric view of the 96-well plate 100d of FIG. 21a;

FIG. 22 is a plan view of the upper surface of a 386-well plate having samples transferred thereto from the four 96-well plates of FIGS. 18a–21c, wherein the unique color indicia of each 96-well plate has been transferred to the respective quadrant of wells in the 384-well plate for tracking proper transfer of samples in accordance with the principles of the present invention.

DETAILED DESCRIPTION OF THE INVENTION

Figure 1:
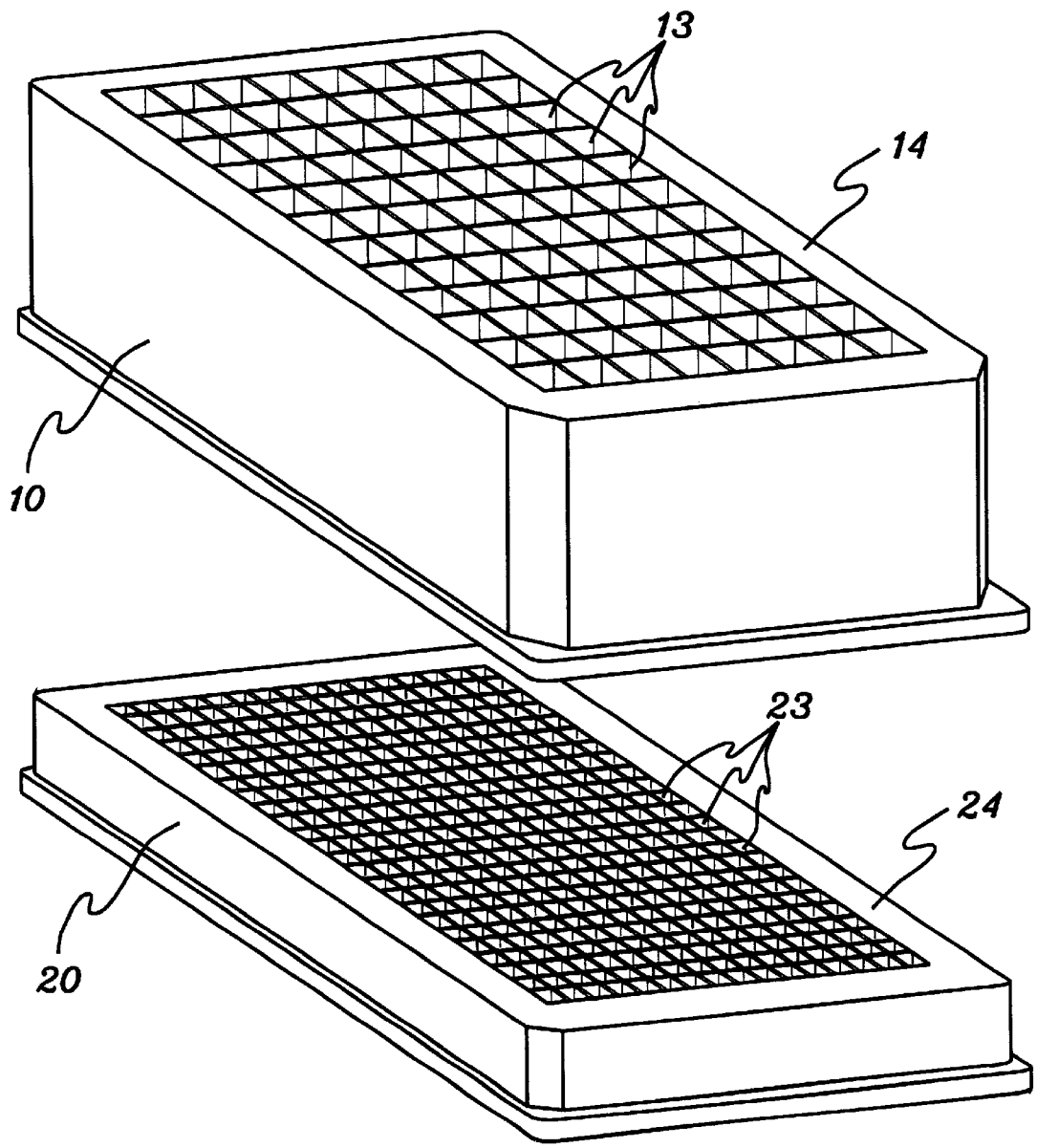
FIG. 1 is an exploded isometric view of a multiwell multiplate stack in accordance with the principles of this invention.
Figure 2:
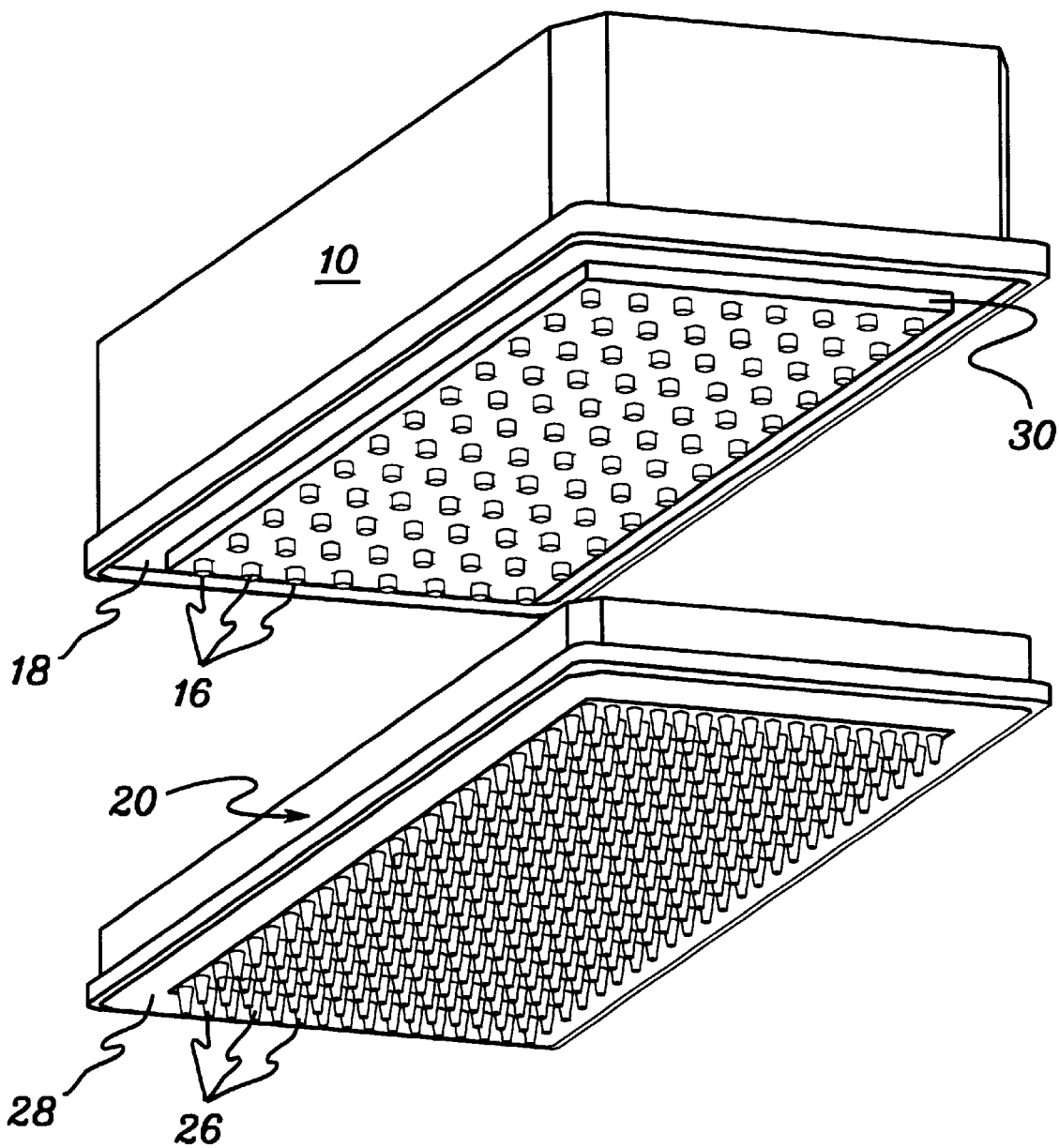
FIG. 2 is a further exploded isometric view of the multiwell multiplate stack of FIG. 1 showing the lower surfaces of the multiwell plates.
Figure 3:
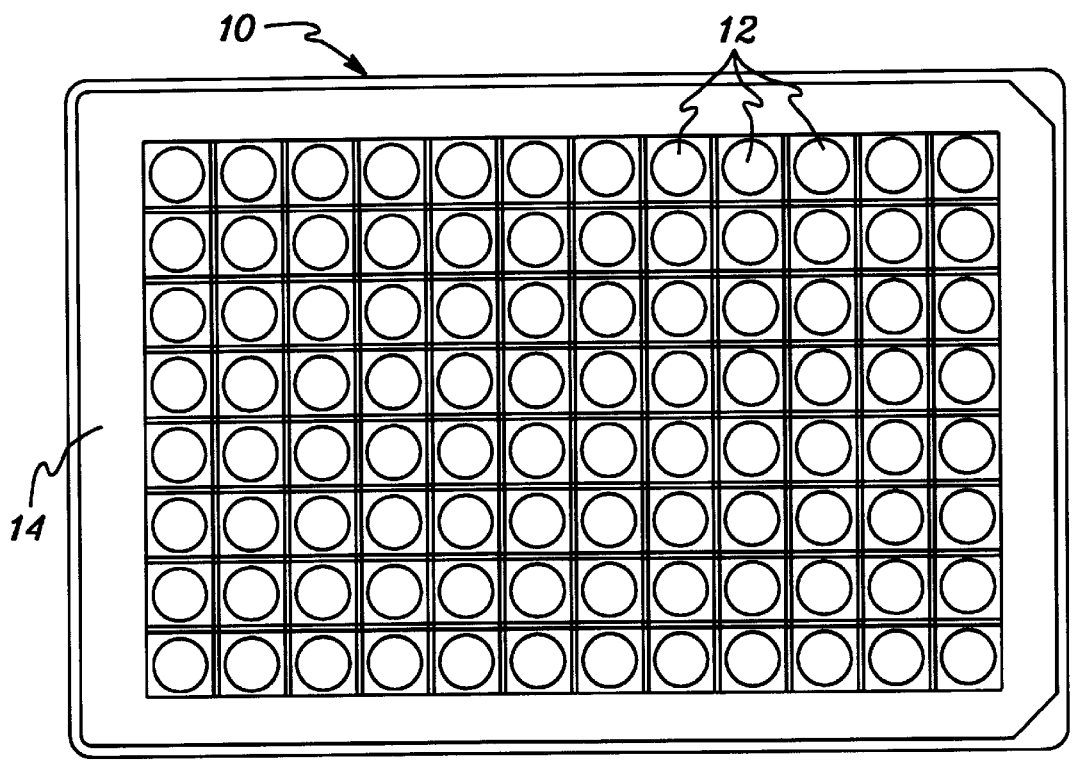
FIG. 3 is a plan view of the upper surface of the 96-well plate of the embodiment of FIGS. 1 & 2.
Figure 4:
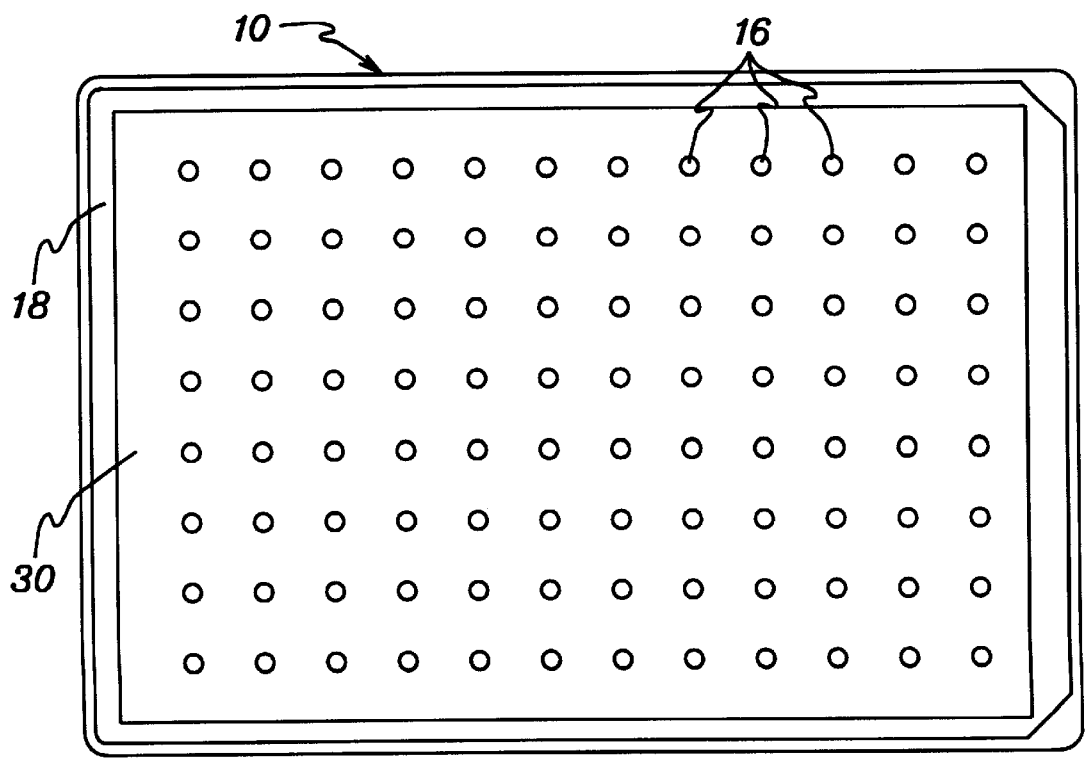
FIG. 4 is a plan view of the lower surface of the 96-well plate of the embodiment of FIGS. 1 & 2.
Figure 5:
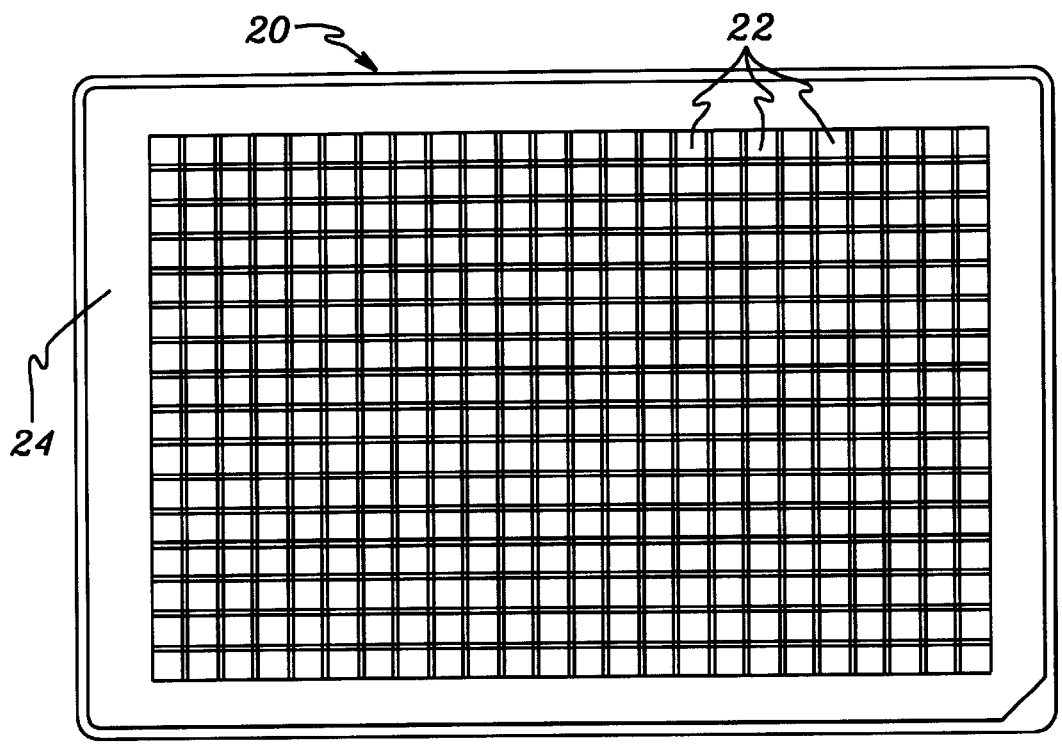
FIG. 5 is a plan view of the upper surface of the 384-well plate of the embodiment of FIGS. 1 & 2.
Figure 6:
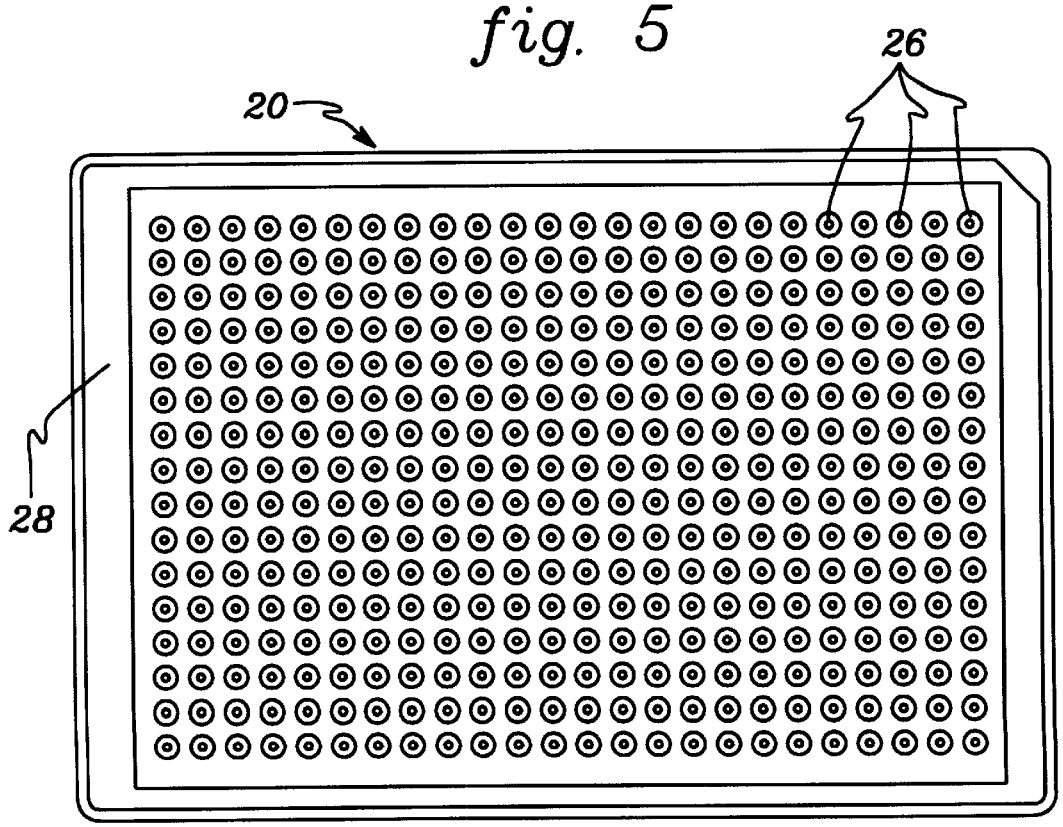
FIG. 6 is a plan view of the lower surface of the 384-well plate of the embodiment of FIGS. 1 & 2.
Figure 7:
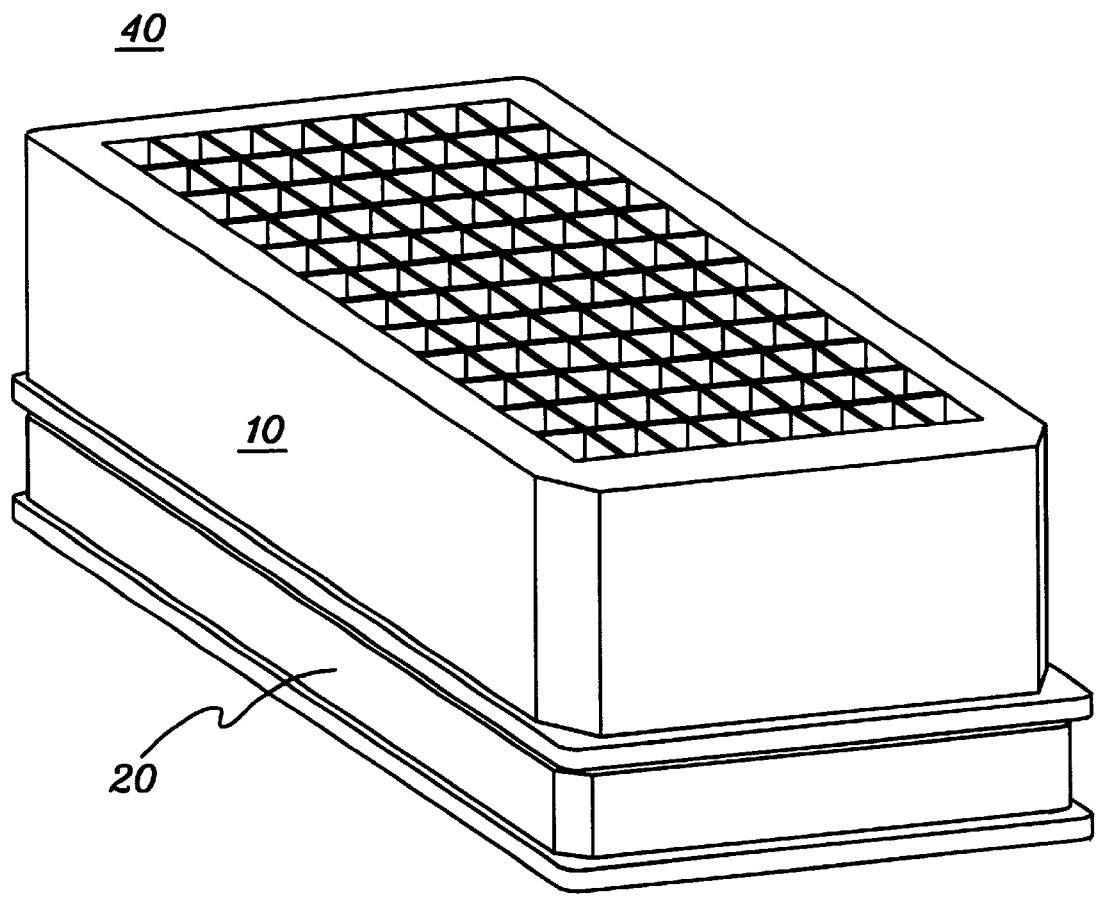
FIG. 7 is an isometric view of the multiwell multiplate stack in accordance with the principles of the present invention.

Generally stated, this invention comprises a technique for processing samples, such as biological, chemical or biochemical samples wherein a multiplate stack comprising two or more plates is defined, within and through which samples are transferred. FIGS. 1–7 present a detailed example of two multiwell plates employed pursuant to this invention. A first multiwell plate 10 comprises a 96-well plate and a second multiwell plate 20 is a 384-well plate, which has exactly four times the number of wells as the 96-well plate.

In many operations, it is desirable to transfer fluid from a 96-well plate to a 384-well plate. These operations include, but are not limited to, the transfer of crude plasmid preparation after cell lysis and precipitation of proteins and genomic DNA, which is typically 400 µl of material. This culture sample size conventionally requires a 96-well plate since the well volume in a 384-well plate is too small. Further, processing typically requires the transfer of this material to a 384-well plate, which may contain a quantity of between 5 µl and 150 µl of high capacity anion exchange resin, such as, e.g., Q HyperD 20 µm. Transfer of material from a 96-well plate to a 384-well plate is today accomplished by pipetting the samples from the first test plate to the second test plate.

Since the 384-well plate has exactly 4× the number of well as the 96-well plate, and since the size and aspect ratio of the two plates can be made similar, then in accordance with the present invention a 96-well plate 10 with flow directors or outlets 16 (FIG. 2) can be produced for direct stacking atop a 384-well plate. The flow directors 16 direct the sample flow from the 96-well plate to one set of wells of the 384-well plate (i.e., one quadrant of wells). Again, this requires proper sizing and aspect ratio for the flow directors 16 of the 96-well plate to align or register with a respective set or quadrant of wells of the 384-well plate.

Pursuant to another feature of the present invention, the 96-well plate 10 can comprise a filter plate so that when stacked atop, for example, a 384-well plate, sample material can be filtered simultaneous with direct transfer thereof from the 96-well plate to the 384-well plate. Still another aspect of this invention is the concept that samples in the 96-well plate are drawn into and through wells in the 384-well plate. This can be facilitated via an appropriate vacuum manifold coupled to the lower surface of the 384-well plate as explained further herein. If desired, the 384-well plate may contain a chromatographic media to separate or purify the sample as it is being drawn through the 384-well plate.

In accordance with the principles of the this invention, a sealing mechanism, such as gasket 30 (FIG. 2), is preferably provided so that when multiwell plate 10 is stacked atop multiwell plate 20, material can be transferred from plate 10 to the selected set of wells of the 384-well plate 20 without contaminating or drying out open wells of the 384-well plate, which as noted may contain purification media. An "open well" comprises a well of the 384-well plate not having a drip director 16 of the 96-well plate aligned therewith when the 96-well plate is stacked atop the 384-well plate.

Referring now more specifically to FIGS. 1–6, first multiwell plate 10, comprising a 96-well plate, has a plurality of wells 13 arrayed in a regular rectangular array with openings 12 thereto in an upper surface 14. Each well has a corresponding drip director 16 in a lower surface 18 of the multiwell plate 10. Similarly, the second multiwell plate 20, which in this example comprises a 384-well plate, has a plurality of wells 23 also arrayed in a regular rectangular pattern each of which has an opening 22 in an upper surface 24 of plate 20. In accordance with this invention, drip directors or outlets 26 also depend downwardly from a lower surface 28 of plate 20.

As noted, a significant feature of this invention is the ability to transfer material from plate 10 directly into plate 20 while simultaneously filtering the material. With conventional pipetting this is not possible. Further, because the volume of each well 13 in 96-well plate 10 is conventionally greater than the volume of each well 23 in 384-well plate 20, this invention teaches the drawing of material into and from the respective wells of the 384-well plate simultaneous with transfer of the material from the 96-well plate. Thus, separation or purification of media drawn into a set of wells of the 384-well plate is also simultaneously accomplished with transfer of the samples from the 96-well plate. To restate, this invention provides for the direct transfer of samples from a first well plate, such as a 96-well plate, to a second well plate, such as a 384-well plate, while simultaneously filtering the sample and purifying the resultant material. This is accomplished notwithstanding that each well of the 96-well plate 10 might hold 400 $\mu$l of sample while the receiving well 23 in the 384-well plate 20 might only hold 120 $\mu$l.

Figure 16:
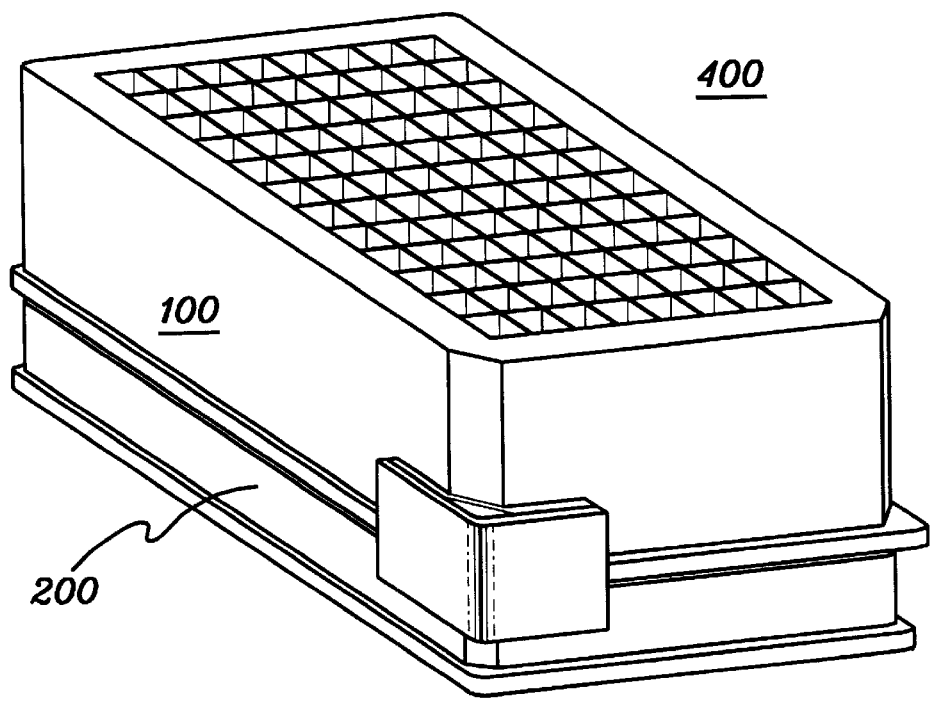
FIG. 16 is an isometric view of an alternate embodiment of the multiwell multiplate stack in accordance with the principles of the present invention wherein an alignment guide is affixed to one corner of the 96-well plate such that the 96-well plate registers with a selected quadrant of wells of the 384-well plate.
Figure 17:
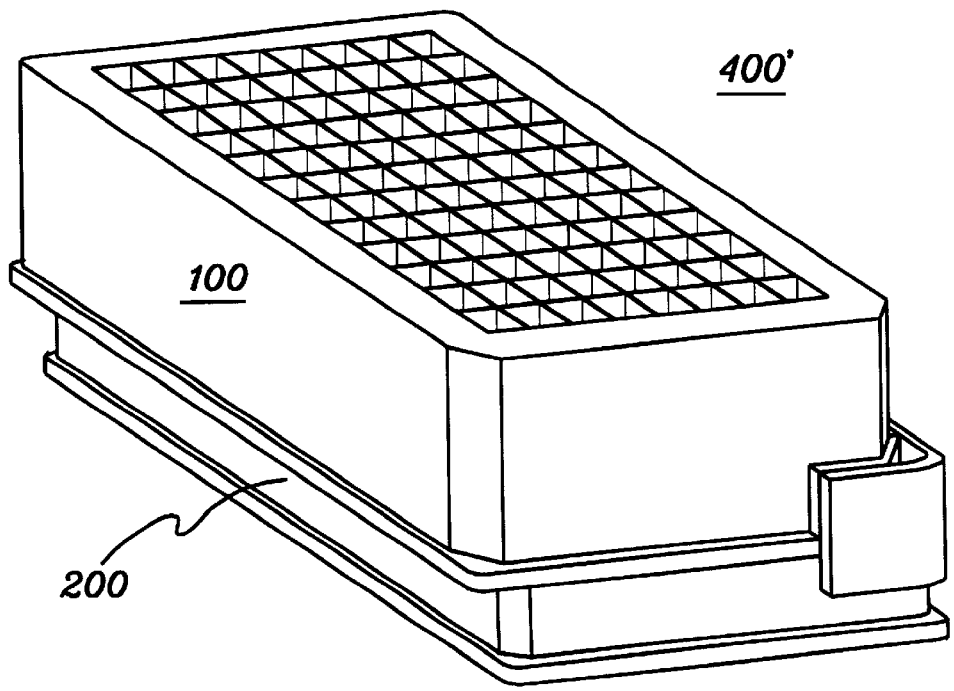
FIG. 17 is an isometric view of another embodiment of the multiwell multiplate stack of FIG. 16 wherein the alignment guide affixed to the 96-well plate is disposed at a different corner of the 96-well plate such that the 96-well plate registers with a different quadrant of wells in the 384-well plate.

When this process is completed, another 96-well plate can be used to address another set of wells from the three remaining sets or quadrants of wells in the 384-well plate 20. This is accomplished by aligning the flow directors of this second 96-well plate with the openings of a different set of wells of the 384-well plate. The second 96-well plate can register, for example, with the appropriate wells by manually aligning the plates, or by employing a set of alignment guides on the respective plates as shown in FIGS. 16 and 17 and described below. Alternatively, an apparatus could be constructed which allows for four different alignment positions of a 96-well plate over the 384-well plate, or four different 96-well plate embodiments could be configured, each with a different alignment of flow directors. With respect to this latter option, a first 96-well embodiment might have its array of flow directors offset to align with a first quadrant of wells of a 384-well plate, while second, third and fourth embodiments would have similar arrays of flow directors on their lower surface each offset to allow facile alignment to a particular quadrant of wells of the 384-well plate.

Note that this invention does not require the use of either a 96-well plate or a 384-well plate. Preferably, however, the first well plate has x number of wells of a certain volume and the second well plate has y number of wells of a different volume, with the well volume of the first well plate being greater than that of the second well plate and with the number of wells in the second well plate being greater than that of the first well plate. More specifically, the number of wells in the second well plate is preferably a multiple of the number of wells in the first plate. Thus, the second well plate can be employed to receive samples from two or more first well plates. This capability further enhances the transfer, filtration and purification processes in accordance with the present invention. Thus, those skilled in the art will understand that the 96-well plate and 384-well plate are discussed herein by way of specific example only and other multiwell plates can be employed without departing from the scope of the present invention as defined by the claims appended herewith.

Since in this example three out of four wells will comprise open wells (i.e., be unused) during the stacking of one 96-well filter plate atop a 384-well plate, these open wells could become dry during the transfer process if they include a separation or purification media. Further, these wells could be subject to cross-contamination from material being transferred to the selected quadrant of wells of the 384-well plate. In order to prevent this, a stack assembly in accordance with this invention has a mechanism for sealing the non-used or open wells of the 384-well plate 20 during the transfer of material from the 96-well plate 10 to the 384-well plate. As one embodiment, gasket 30 (FIG. 2) is affixed to the bottom surface 18 of each 96-well plate 10 having material to be transferred to the 384-well plate. Gasket 30 fills the space between drip directors 16 depending from the 96-well plate. Thus, when the 96-well plate is aligned over a respective set of wells of the 384-well plate, gasket 30 will automatically cover open wells of the 384-well plate to prevent cross-contamination of the wells during transfer of material to the selected well set and/or to prevent the drawing of air through the open wells when a vacuum is applied to the outlets of the 384-well plate, thereby preventing drying of the wells. The gasket may be fabricated, for example, of a closed-cell foam material or rubber.

Figure 8:
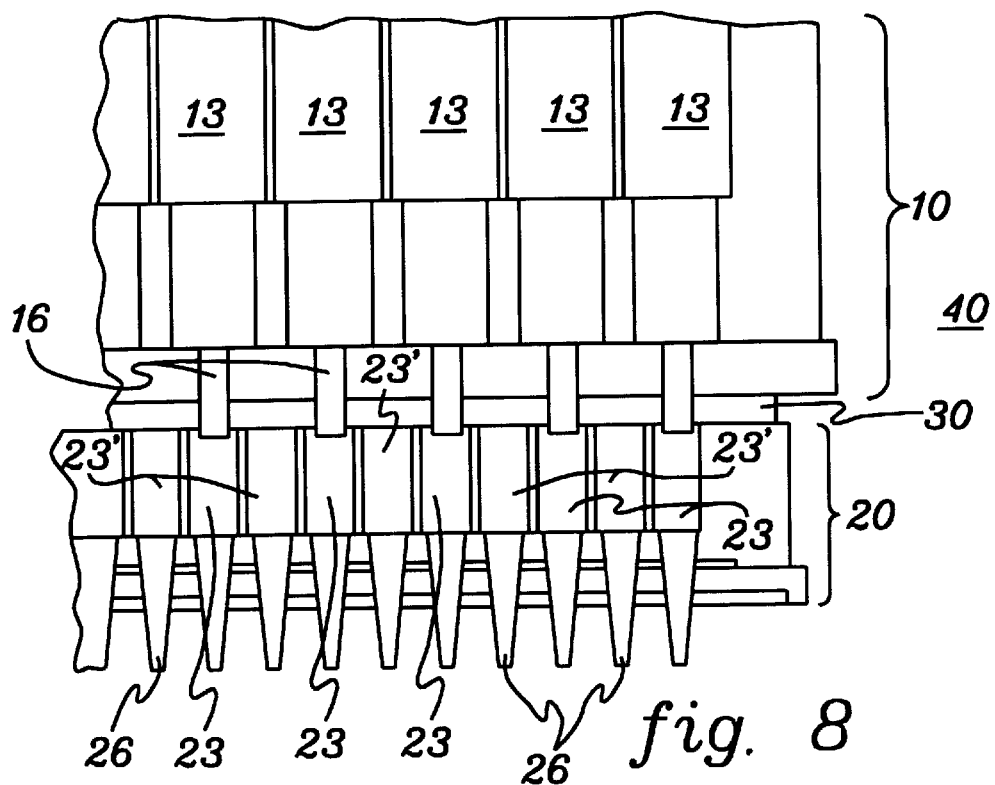
FIG. 8 is a partial cross-sectional view of one embodiment of the multiwell multiplate stack of FIG. 7 showing a first 96-well plate 10 disposed over a first set of wells of the 384-well plate.
Figure 9:
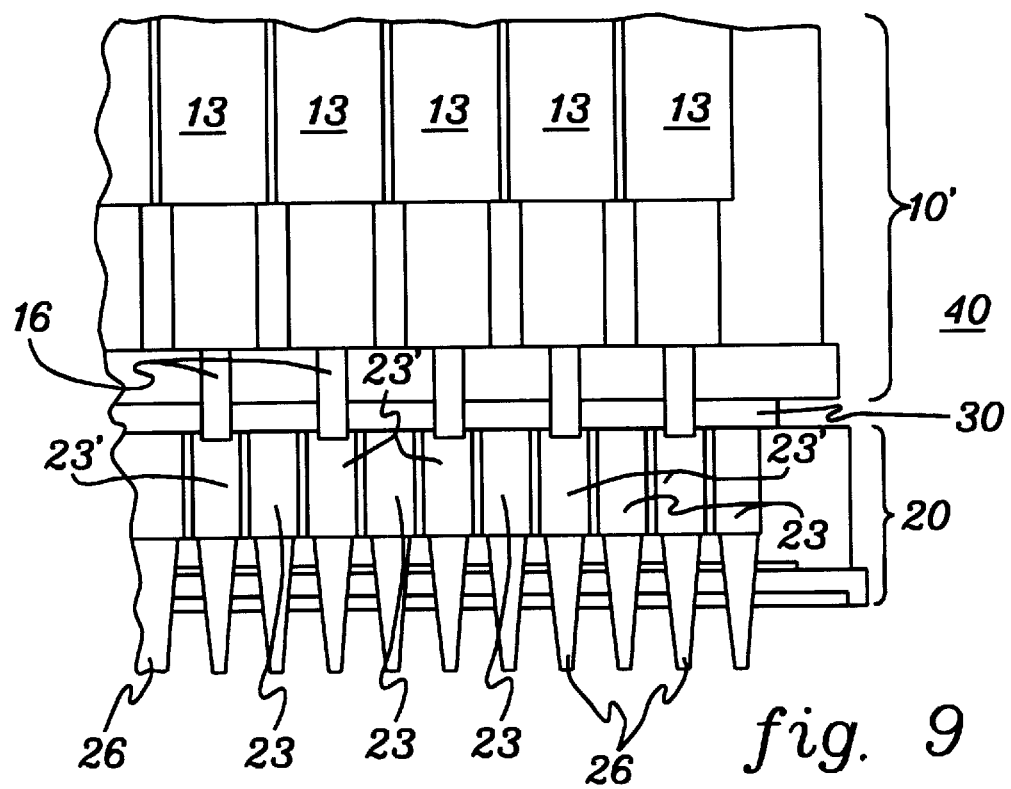
FIG. 9 is a partial cross-sectional view of one embodiment of the multiwell multiplate stack of FIG. 7 showing a second 96-well plate 10' disposed over a second set of wells of the 384-well plate.

In accordance with the present invention, FIGS. 8 & 9 depict partial cross-sectional views of a first 96-well plate 10 and a second 96-well plate 10', respectively, disposed over different sets of wells 23 & 23' in a 384-well plate 20. As shown, drip directors 16 register with and depend into corresponding wells 23,23' in the 384-well plate 20 when the 96-well plates 10,10' are stacked atop the 384-well plate. Gaskets 30 affixed, for example, to the lower surface of each 96-well plate 10,10', serve to seal the open wells 23 or 23' in the 384-well plate during transfer of material from the respective wells 13 of the 96-well plates 10,10' as described above.

Figure 10:
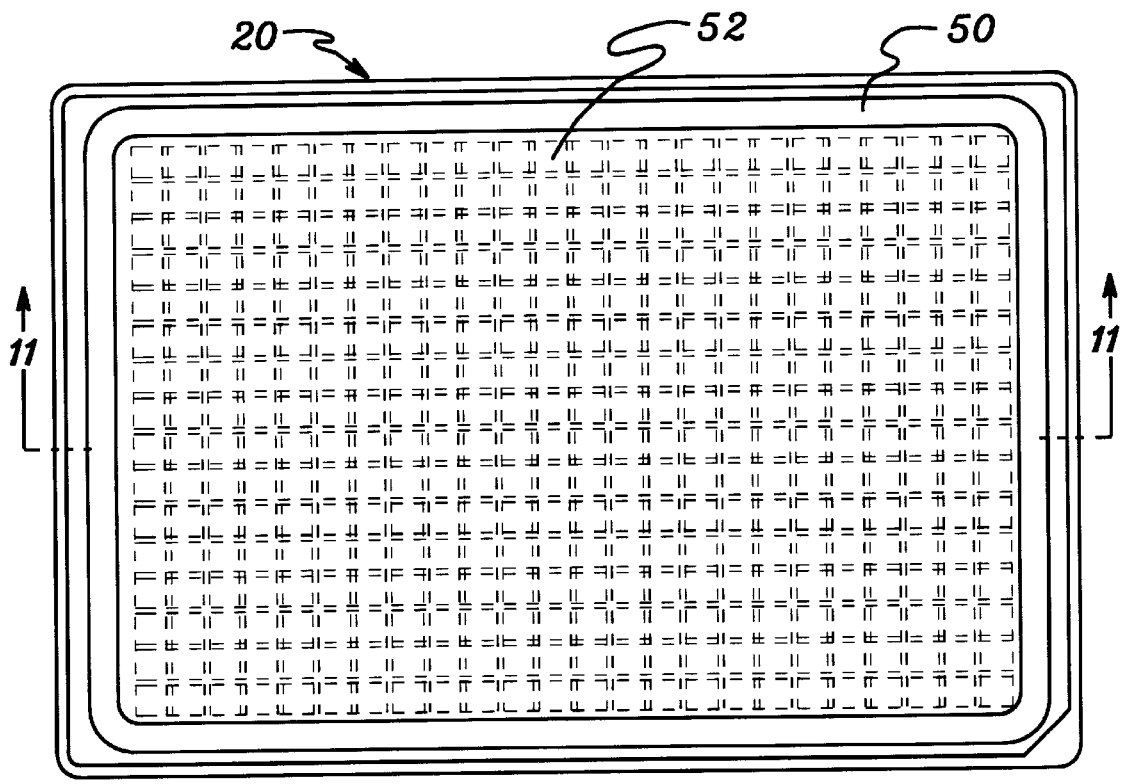
FIG. 10 is a plan view of the upper surface of the 384-well plate showing an alternate sealing mechanism employing an O-ring and a puncturable membrane across the upper surface of the 384-well plate.
Figure 11:
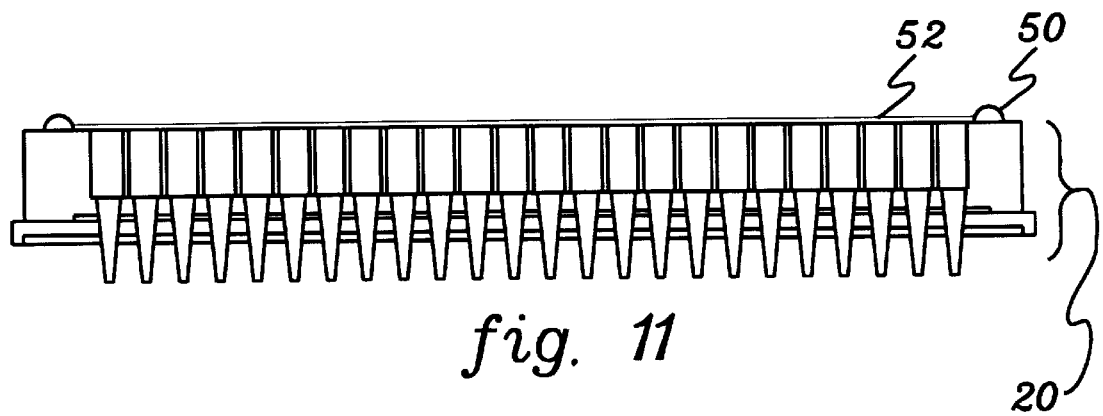
FIG. 11 is a cross-sectional view of FIG. 10 taken along line 11—11.

An alternate embodiment of a sealing mechanism pursuant to this invention is depicted in FIGS. 10 & 11. This approach comprises an O-ring or rim gasket 50, which may be disposed atop the 384-well plate as shown, or conceivably could comprise a separate structure from the 384-well plate. If comprising a separate structure, gasket 50 would be stacked as shown atop the 384-well plate prior to placement of a 96-well plate thereon for transfer of fluid between plates. Gasket 50 operates to seal the ambient atmosphere from the interior region between the 96-well plate (not shown) and the 384-well plate so that when a vacuum is applied to outlets 26 of the 384-well plate, air will not be drawn through open wells of the plate and cause drying of the wells.

As an enhancement, the 384-well plate could be fitted with a flexible, puncturable membrane 52 so that when the flow directors of a 96-well plate are placed in registration with a corresponding set of wells 23,23' of the 384-well plate, the flow directors will puncture membrane 52 to allow transfer of material from the 96-well plate to the 384-well plate, with the balance of membrane 52 operating as a gasket which covers the openings to the unselected wells.

Figure 12:
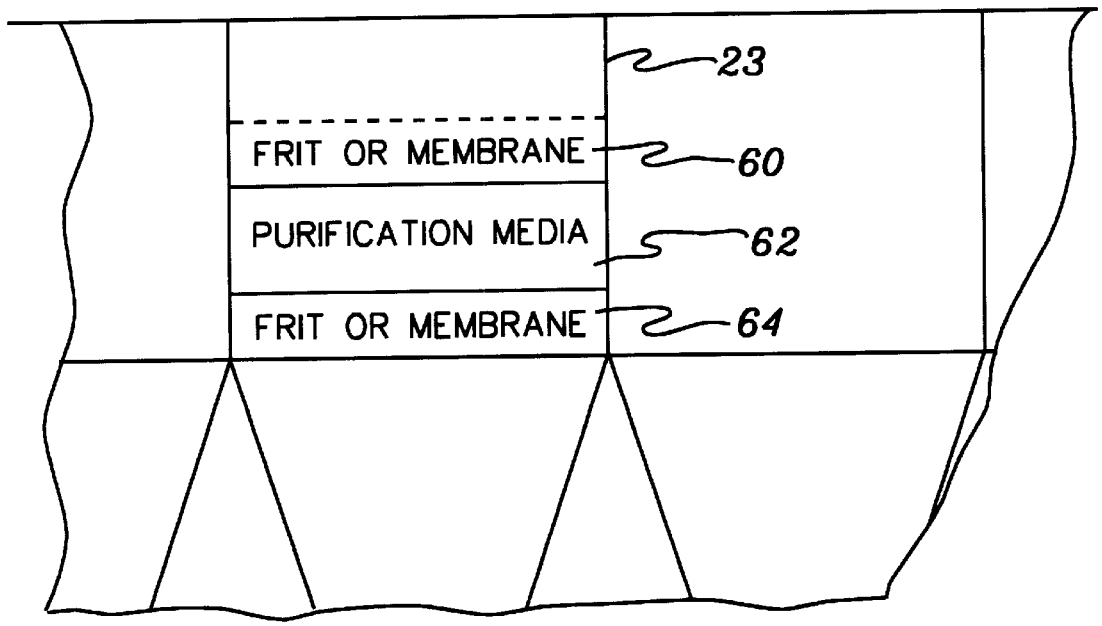
FIG. 12 is a fragmentary, enlarged cross-sectional view of one embodiment of a well of a 384-well plate in accordance with the present invention containing a purification or separation media.

As a variation or further option, the amount of air passing through the open wells in the 384-well plate may be further reduced by providing a wetted porous material such as a membrane or frit 60 atop, for example, a purification media 62 packed in each well 23 as shown in FIG. 12. Media 62 is disposed over an additional frit 64 placed in the bottom end of each well. Frit or membrane 60 is assumed to have a pore size fine enough so that when wetted it does not allow air to easily pass through. For example, pore sizes for frit 60 could be between 0.1 $\mu$m and 10 $\mu$m. As a further advantage to this enhancement, provision of a porous material such as a frit or membrane on top of the purification media within the wells of the 384-well plate also serves to distribute more evenly by capillary action any reagent added, such as an elution buffer. This is particularly noticeable when a relatively small volume of buffer is used.

Figure 13:
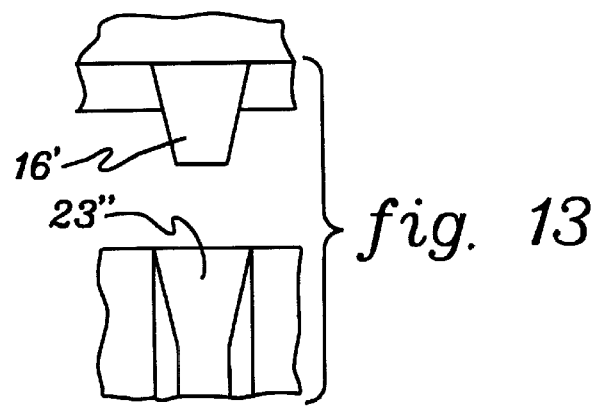
FIG. 13 is a fragmentary, enlarged cross-sectional view of a drip director 16' of an upper well plate configured to mesh with an inlet 23" of a corresponding well of a lower well plate in a multiwell multiplate stack.

FIG. 13 depicts a still further enhancement wherein sealing between the outlets or drip directors 16 (FIG. 2) of the 96-well plate and corresponding wells of a quadrant of the 384-well plate can be achieved by configuring each drip director 16' to tightly mesh with an inlet 23" of a corresponding well of the 384-well plate when the 96-well plate is placed atop the 384-well plate. By so configuring each outlet 16' of the top plate and inlet of the receiving plate, an improved seal between the wells of the 96-well plate and the 384-well plate is achieved to prevent cross-contamination of wells during transfer of material from the 96-well plate to the 384-well plate.

Figure 14:
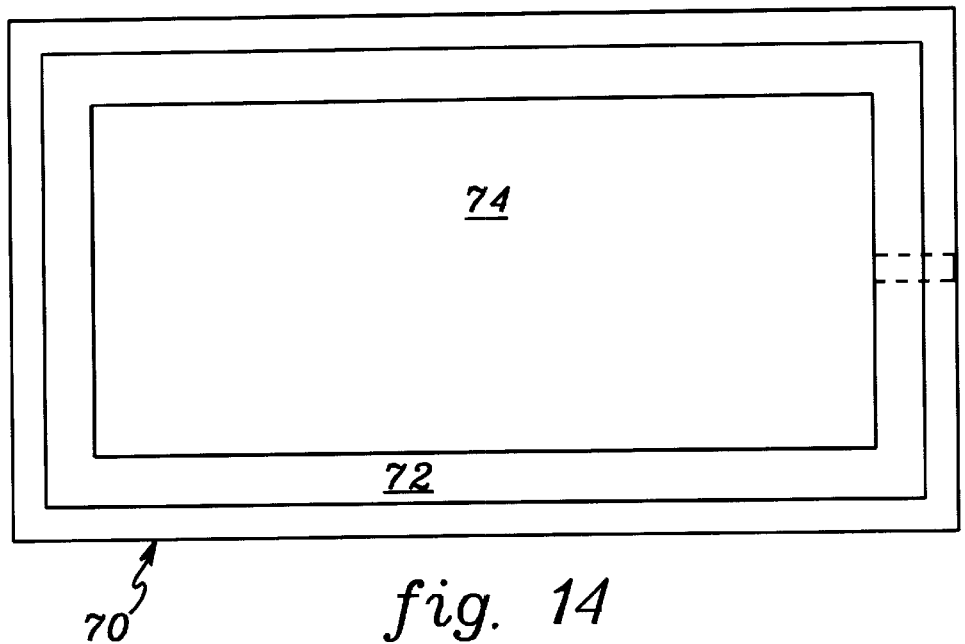
FIG. 14 is a plan view of the upper surface of one embodiment of a vacuum manifold configured, for example, to receive the lower surface of the 384-well plate of the stack of FIG. 7.
Figure 15:
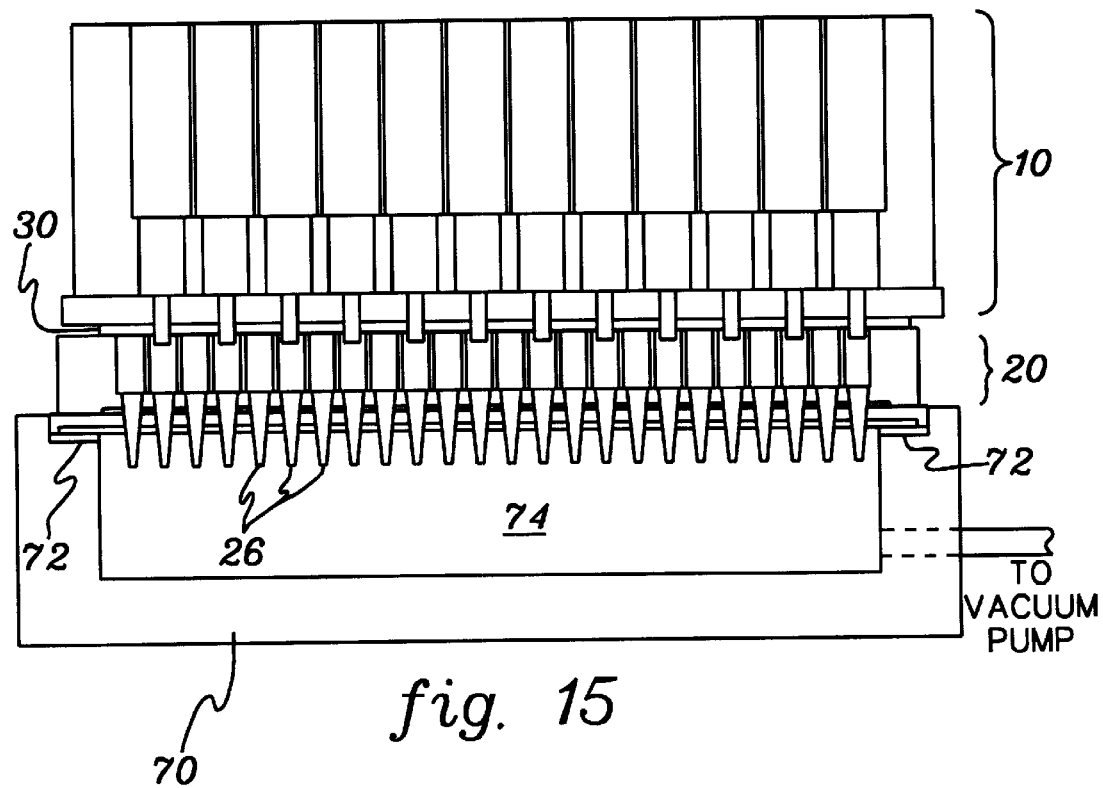
FIG. 15 is a cross-sectional view of one embodiment of the multiwell multiplate stack of FIG. 7 disposed atop the vacuum manifold of FIG. 14 in accordance with the present invention.

As noted above, transfer of material from the 96-well plate to the 384-well plate is facilitated by the application of a vacuum at outlets 26 of the 384-well plate 20. FIG. 14 depicts a top plan view of a vacuum manifold configured and sized to receive the lower surface of the 384-well plate, while FIG. 15 depicts a cross-sectional view of a multiplate stack in accordance with the present invention disposed atop vacuum manifold 70 of FIG. 14. Manifold 70 is designed to readily seal to the lower surface of the 384-well plate when the stack is disposed thereon. For example, a gasket 72 could be provided along an appropriately sized shelf in manifold 70. Liquid transferred from the 96-well plate into and through the 384-well plate can be removed into a collection well 74 in manifold 70.

Also as noted above, alignment of the first multiwell plate atop the second multiwell plate can be facilitated by incorporating an alignment guide on either the first plate or the second plate. FIGS. 16 & 17 depict different implementations of an alignment guide affixed to a 96-well plate 100 such that the 96-well plate registers with a different quadrant of wells in a 384-well plate 200. In FIG. 16, the alignment guide is secured to a first corner of the 96-well plate so that a multiwell stack 400 is produced wherein the flow directors of the 96-well plate 100 automatically align to a first set of wells in the 384-well plate 200, and in FIG. 17 the alignment guide is affixed to a different corner of the 96-well plate 100 so that a different alignment within the multiwell stack 400' is automatically produced when the 96-well plate is placed atop the 384-well plate. Those skilled in the art will understand that automatic alignment to one quadrant of the remaining quadrants of wells in the 384-well plate can be achieved by affixing an appropriate alignment guide to one of the remaining corners of the 96-well plate. As a variation on the embodiments of FIGS. 16 & 17, the alignment. guides depicted could alternatively be secured to different corners of the 384-well plates such that the 96-well plate could only register with a desired set of wells of the 384-well plates when stacked atop the 384-well plate with a side surface in contact with the alignment guide.

FIGS. 18a–22 depict certain additional enhancements to a multiwell multiplate stack and method for processing biological/chemical samples using the same in accordance with the principles of the present invention. Significant concerns in transferring samples from a first multiwell plate to a second multiwell plate as proposed herein include: (1) insuring consistent and proper alignment of the first multiwell plate over the second multiwell plate; and (2) detecting any cross-talk or cross-contamination of samples from different wells of one or more transferring multiwell plates into one or more wells of the receiving multiwell plate. For purposes of discussion, FIGS. 18a–22 assume that the first (or transferring) multiwell plate comprises a 96-well plate and the second (or receiving) multiwell plate comprises a 384-well plate. However, those skilled in the art will understand that either or both of these well plates may contain a different number of wells arranged in any regular array. Further, note that FIGS. 18a–21c depict the wells of the first multiwell plate as being cylindrical in shape. Alternatively, the square or rectangular-shaped wells of FIGS. 1–17 could be employed.

As an enhancement to the alignment guides depicted in FIGS. 16 & 17, color-coding of each alignment guide on the 96-well plates 100a, 100b, 100c and 100d of FIGS. 18a, 19a, 20a and 21a, and color-coding of the appropriate corner of the 384-well plate 200 with a matching color can be advantageously employed in accordance with the present invention. With color-coding of the alignment guides on the 96-well plates and the corners of the 384-well plate, a user can quickly and easily align each 96-well plate to the 384-well plate and thus the wells of the 96-well plate to the desired quadrant of wells in the 384-well plate without having to track where they are in the aligning sequence. In another embodiment, each of the 96-well plates themselves may be color-coded to match the color of a particular corner of the receiving plate.

Figure 18A:
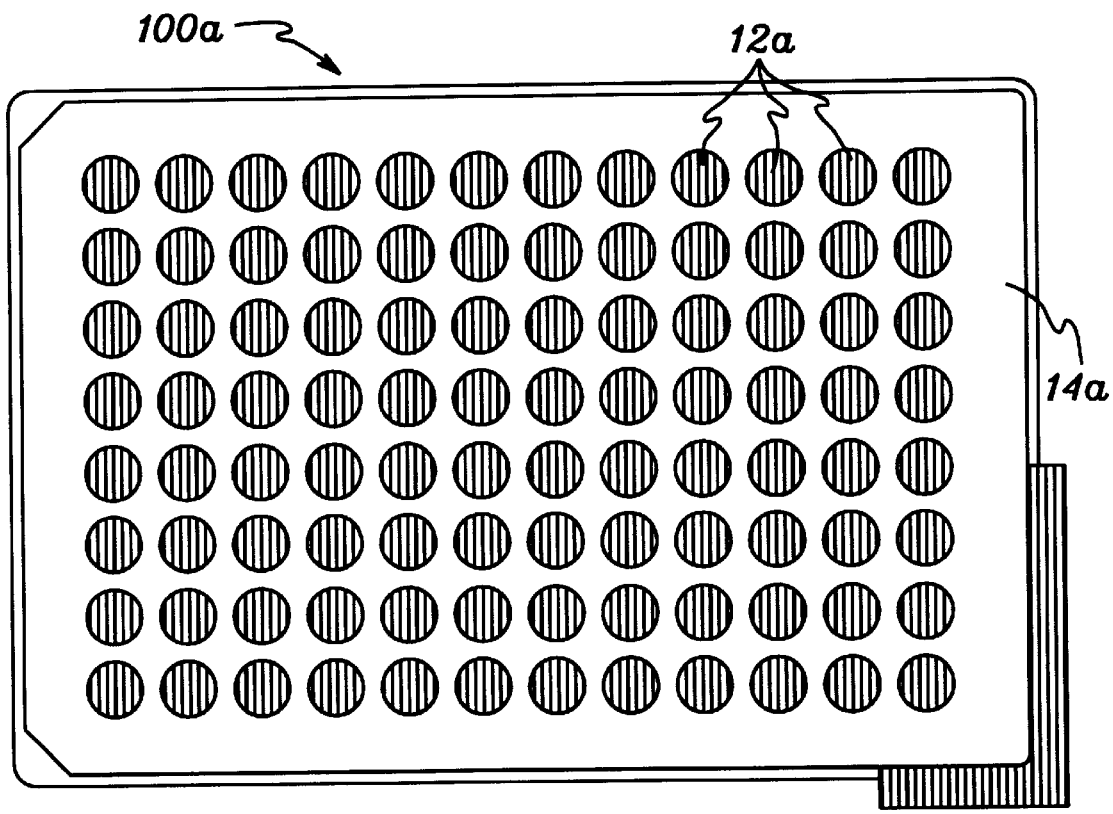
FIG. 18a is a plan view of the upper surface 14a of a 96-well plate 100a comprising an alternate embodiment of the present invention, this embodiment having transfer indicia within the wells and an alignment guide at one corner thereof in accordance with the principles of the present invention.
Figure 18B:
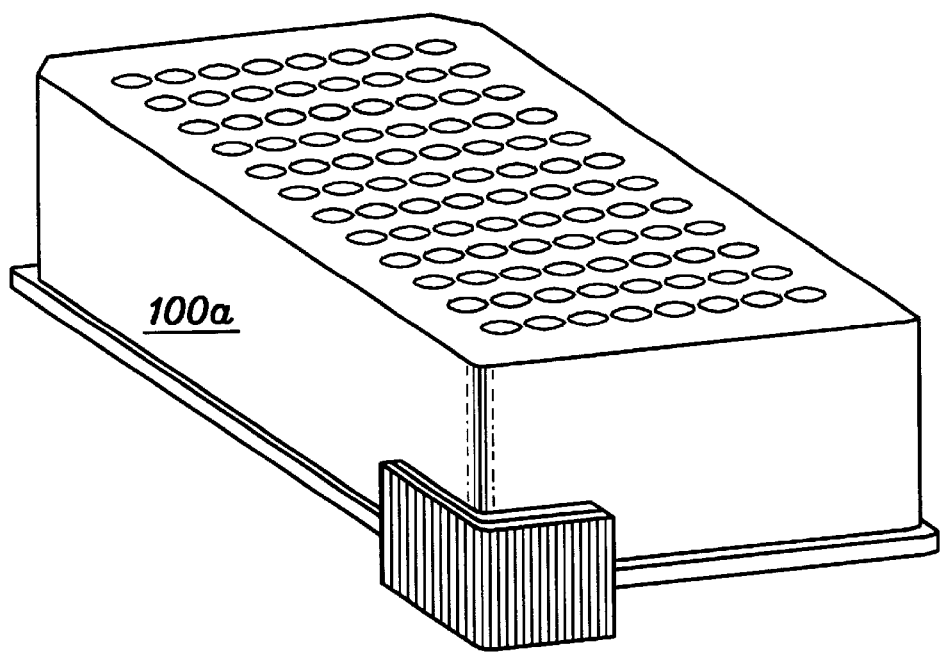
Figure 18C:
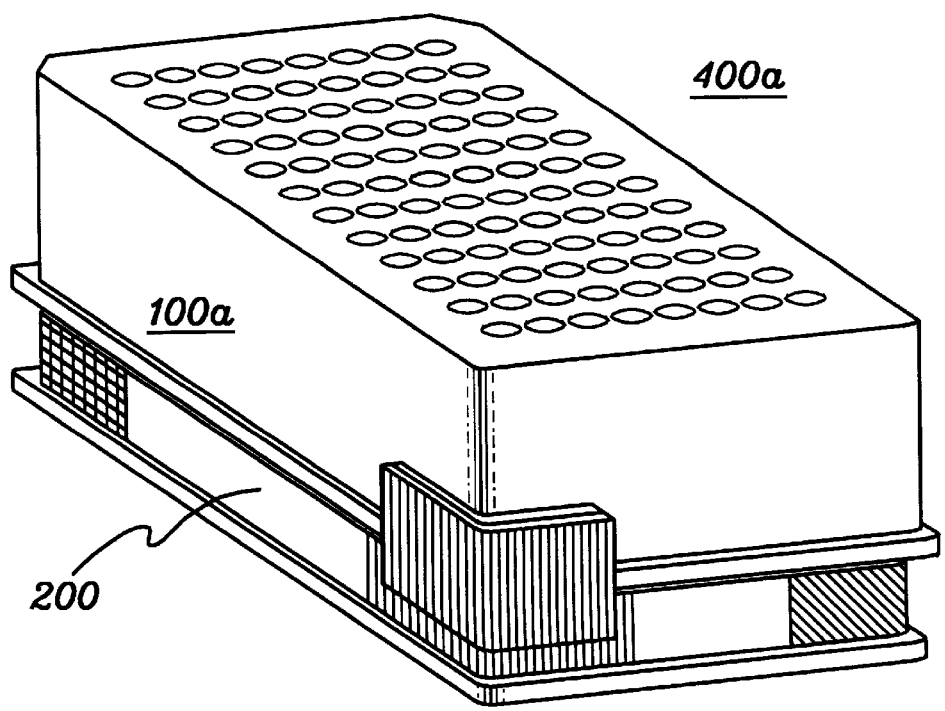
FIG. 18c is an isometric view of the 96-well plate 100a of FIGS. 18a & 18b stacked 400a atop a 384-well plate 200 for transfer of sample from the 96-well plate to the 384-well plate in accordance with the present invention.
Figure 19A:
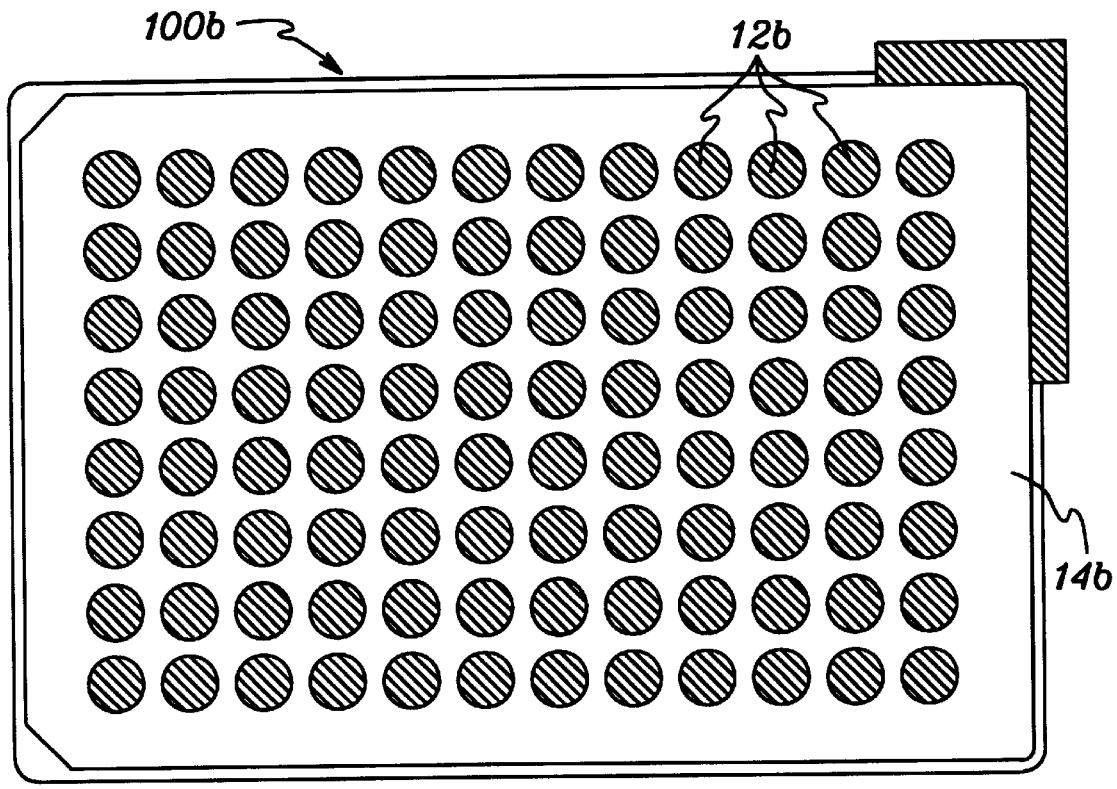
FIG. 19a is a plan view of the upper surface 14b of an alternate embodiment of the 96-well plate 100b of FIGS. 18a–18c wherein a different colored transfer indicia is disposed within the wells of the 96-well plate and the alignment guide is disposed at a different corner for aligning the wells thereof to a different quadrant of wells in the 384-well plate in accordance with the principles of the present invention.
Figure 19B:
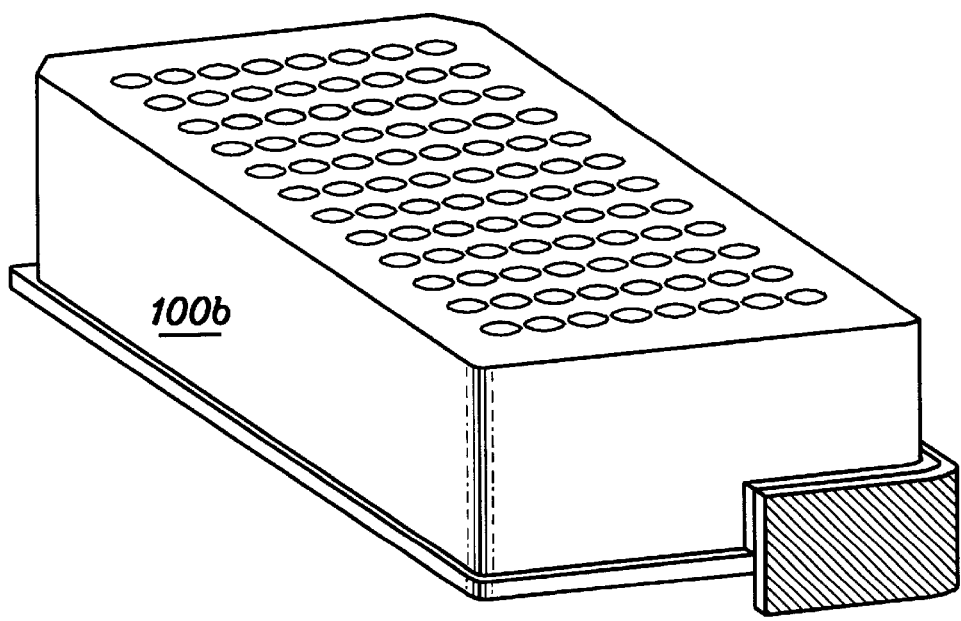
Figure 19C:
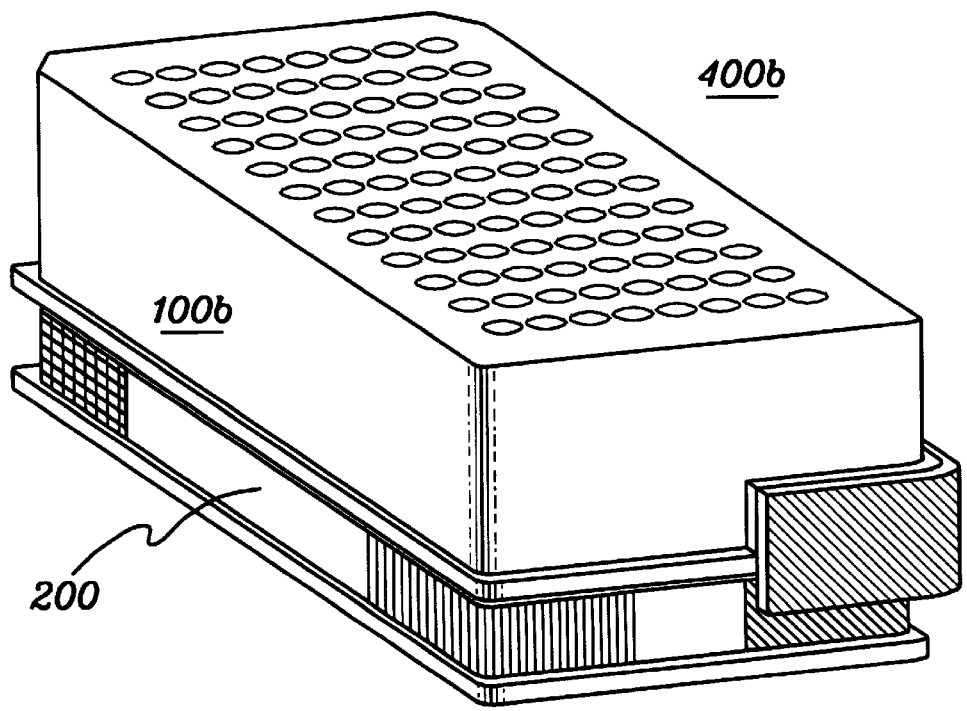
FIG. 19c is an isometric view of the 96-well plate 100b of FIGS. 19a & 19b stacked 400b atop a 384-well plate 200 for transfer of sample from the 96-well plate to the 384-well plate in accordance with the principles of the present invention.
Figure 20A:
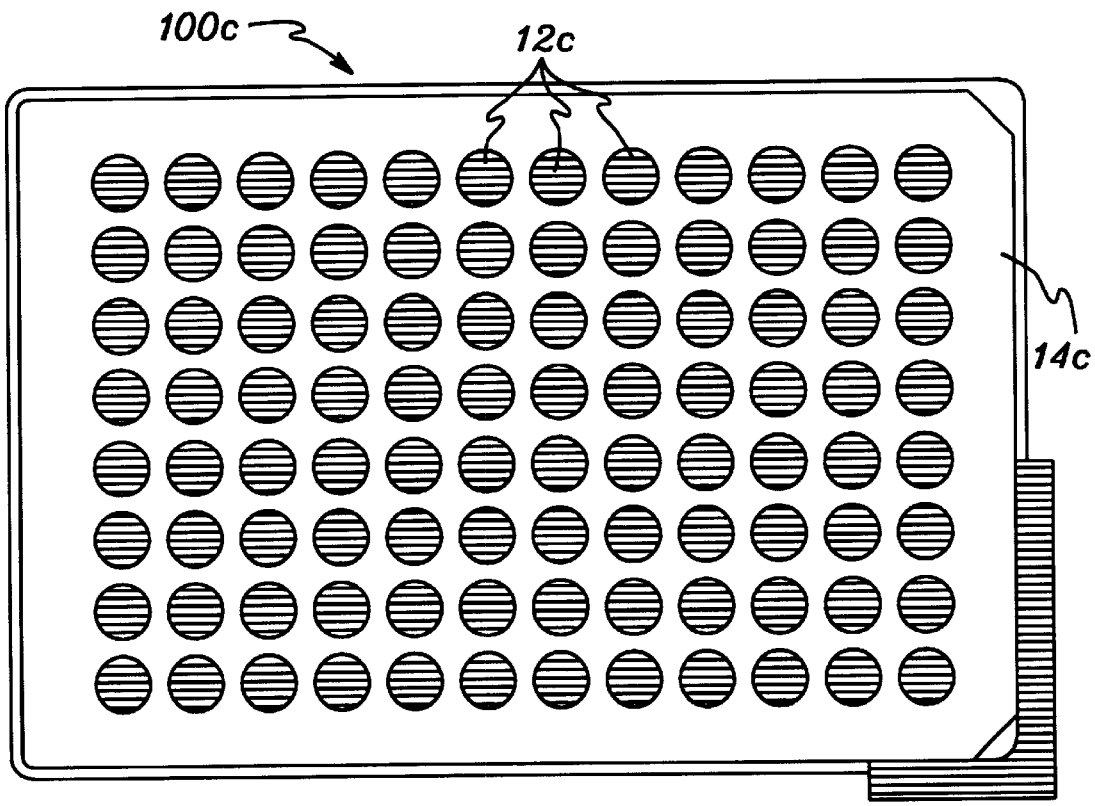
FIG. 20a is a plan view of the upper surface 14c of another embodiment of the 96-well plate 100c of FIGS. 18a–18c wherein a different colored transfer indicia is disposed within the wells of the 96-well plate and the alignment guide is disposed at a different corner for aligning the wells thereof to a different quadrant of wells in the 384-well plate.
Figure 20B:
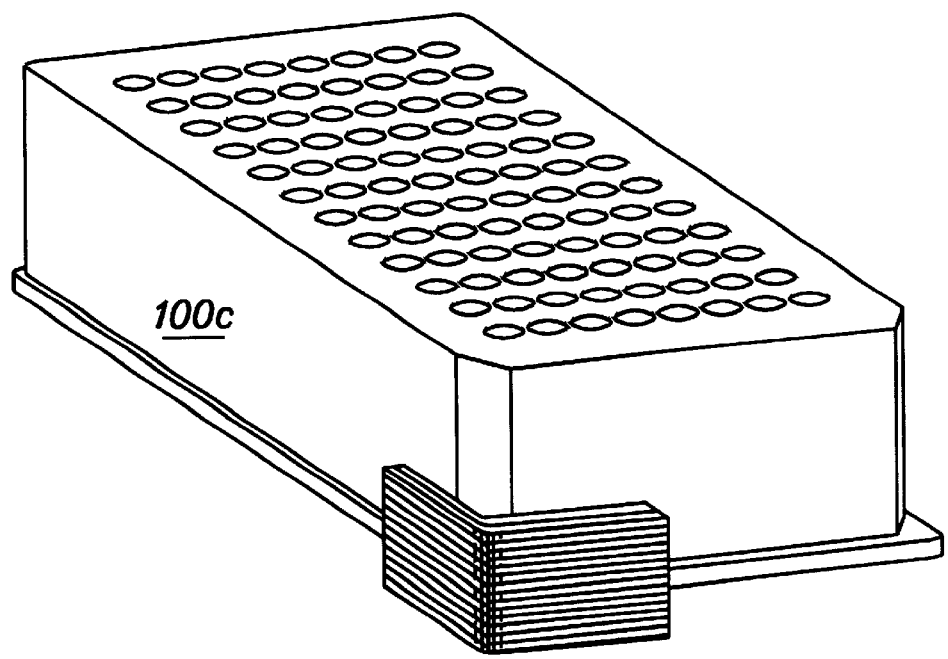
Figure 20C:
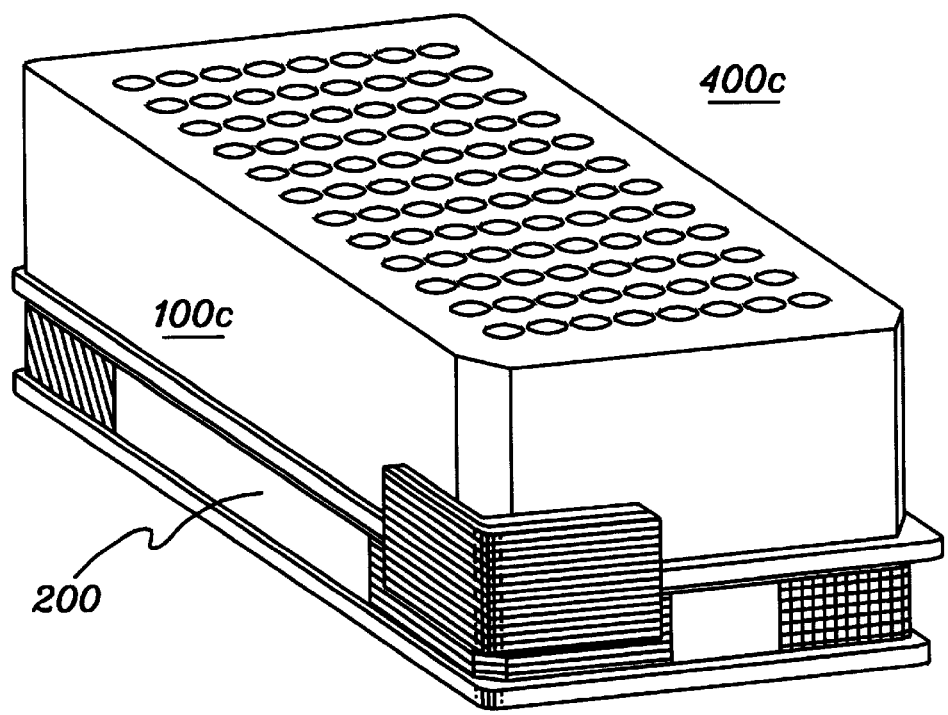
FIG. 20c is an isometric view of the 96-well plate 100c of FIGS. 20a & 20b stacked 400c atop a 384-well plate 200 for transfer of sample from the 96-well plate to the 384-well plate in accordance with the principles of the present invention.
Figure 21A:
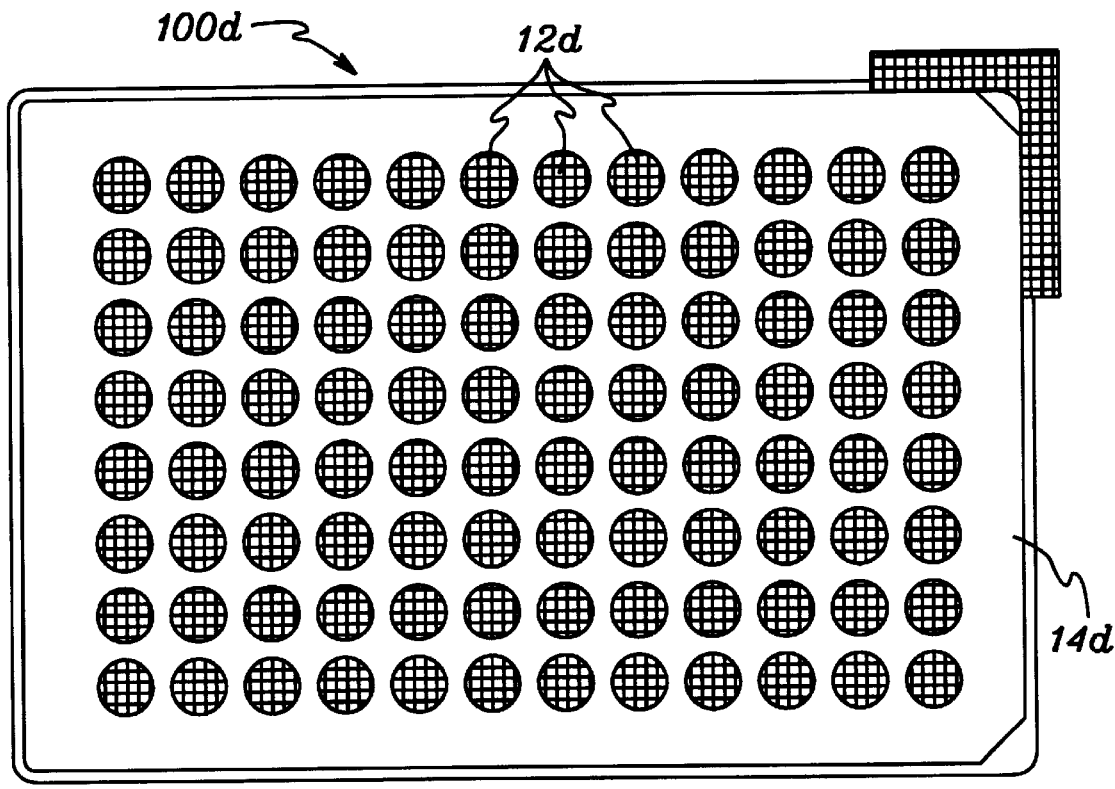
FIG. 21a is a plan view of the upper surface 14d of still another embodiment of the 96-well plate 100d of FIGS. 18a–18c wherein a different colored transfer indicia is disposed within the wells of the 96-well plate and the alignment guide is disposed at a different corner for aligning the wells thereof to a different quadrant of wells in the 384-well plate.
Figure 21B:
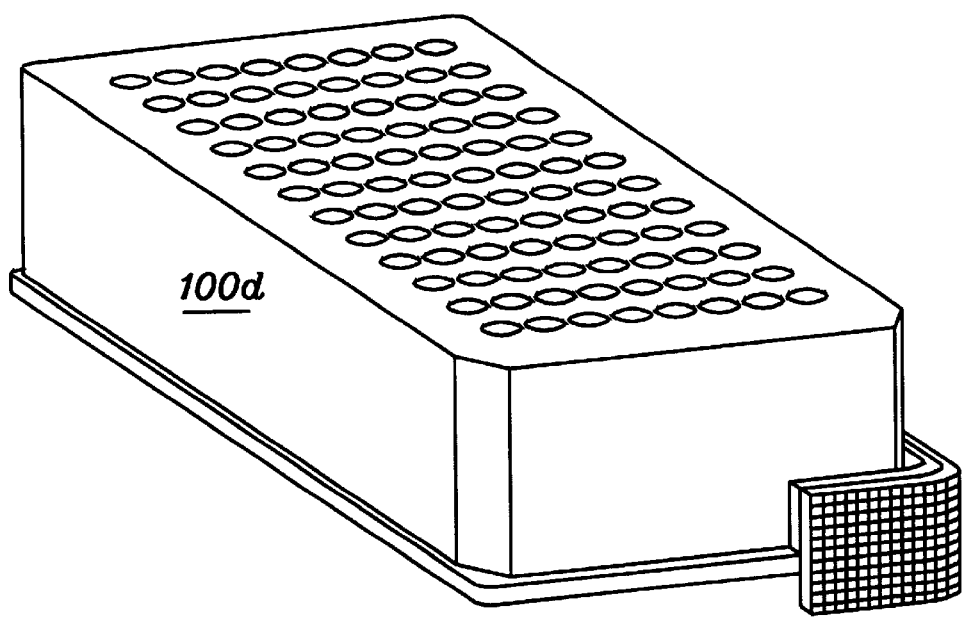
Figure 21C:
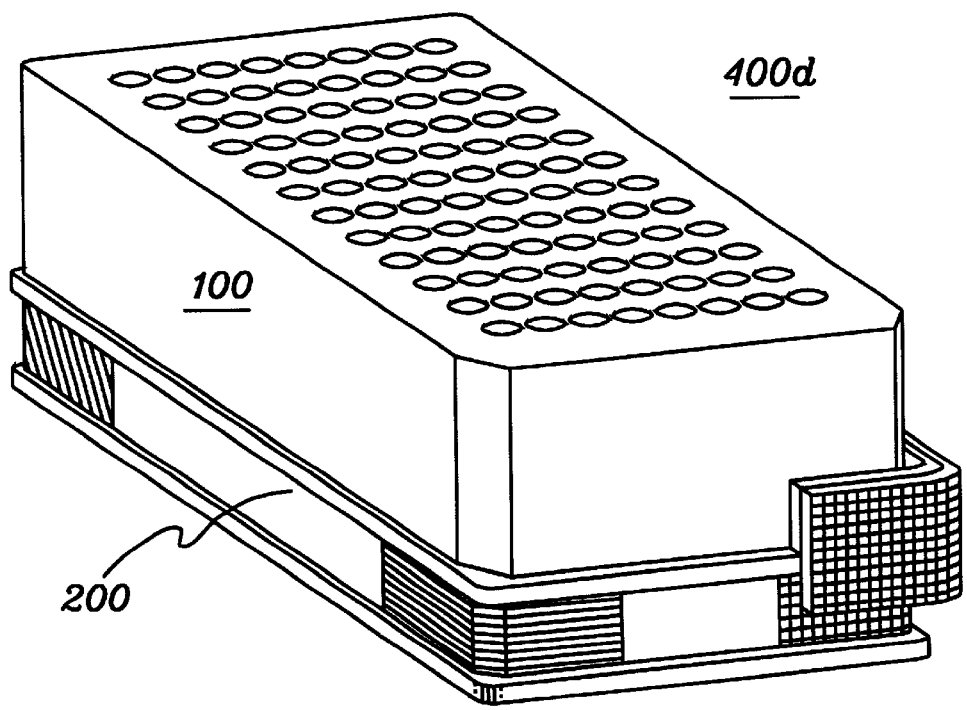
FIG. 21c is an isometric view of the 96-well plate 100d of FIGS. 21a & 21b stacked 400d atop a 384-well plate 200 for transfer of sample from the 96-well plate to the 384-well plate in accordance with the principles of the present invention.

By way of example, FIGS. 18a–18c depict a 96-well plate 100a having a red-coded alignment guide, FIGS. 19a–19c depict a 96-well plate 100b having a green-coded alignment guide, FIGS. 20a–20c depict a 96-well plate 100c having a blue-coded alignment guide and FIGS. 21a–21c depict a 96-well plate 100d having a yellow-coded alignment guide. Correspondingly, the 384-well plate 200 of FIGS. 18c, 19c, 20c and 21c has matching color-coding at each one of the four corners of the 384-well plate. Note that in this example, it is assumed that the shape and size of each 96-well plate and the 384-well plate are similar.

Note also that the colors red, yellow, green and blue are provided for example only and that the claims presented herewith are not limited to any specific color selection. Further, those skilled in the art will note that other alignment indicia besides color could be employed. For example, various positional symbols could be used in association with each 96-well plate and its alignment guide for aligning to corresponding symbols on the 384-well plate. Also, the alignment indicia (although preferably associated with the alignment guide and a corresponding corner of the 384-well plate) could be disposed remotely from the alignment guide and the corresponding corner of the 384-well plate. In addition, the alignment mechanism proposed herein, including the alignment guide and alignment indicia, may be used independent of or in combination with a sealing mechanism as described hereinabove, such as gasket 30 of FIG. 2.

In order for a user to readily determine whether cross-talk has occurred during the various transfer steps, a transfer indicia, such as color-coding of the samples, is used to track transfer of samples from each of the 96-well plates to the 384-well plate. Specifically, the filters 12a, 12b, 12c and 12d in the wells of the 96-well plates of FIGS. 18a, 19a, 20a and 21a can be pre-loaded with a non-toxic, inert colorant, such as food coloring marketed by McCormick's of Hunt Valley, Md. In one embodiment, the 96-well plates comprise filter plates and the pre-loaded colorant is allowed to dry on the filters before introduction of the samples into the 96-well plates. When the 96-well plates are used in a transfer process as described hereinabove, all samples from a particular 96-well plate will be a common color. If there is any deviation from the expected color in a well of the 384-well plate or the color appears in a well outside the subset of wells intended to receive samples from the particular 96-well plate, cross-talk has occurred. In many processes, the presence of food coloring will not interfere with the downstream processing steps performed on the samples, DNA purification processing being one example. As noted, FIGS. 18a, 19a, 20a and 21a respectively depict color-coded filters within the wells of the four 96-well plates. Each of these 96-well plates employs filters with a common, unique color code, and in the embodiment shown, the color coding of the filters matches the color coding of the alignment indicia of the alignment guides. However, this is not a requirement. Also, as an alternative, the color of the entire 96-well plate could match the color coding of the filters contained therein. Further, in certain processes, only a selected well or wells of the 96-well plate may contain a color-coded filter in accordance with this aspect of the present invention.

As a specific implementation, using a multi-channel pipette, 10 µl of red colored solution (comprising, e.g., one drop of food coloring to 30 ml of distilled water) is loaded onto the filters of each well of a 96-well plate, and allowed to dry. This process is repeated with three other 96-well plates using yellow, green and blue solutions to produce the colored filters shown in FIGS. 18a, 19a, 20a and 21a. Samples are then loaded into the wells of the 96-well plates. In accordance with the principles of this invention, these samples are subsequently transferred to a second well plate, for example, a 384-well plate, stepwise. Beginning with the red colored plate, all of the samples transferred from the red plate should be red, and the other wells of the 384-well plate should remain original color. The process is repeated with the yellow plate, and if any cross-talk occurs within the 384-well plate with the previously transferred red samples or the wells expected to be empty, the sample color would change or the wells expected to be empty would turn yellow. Similarly, samples from the green plate are transferred and then the blue plate. Using this method, at any time during the transfer process, the user can readily ascertain whether any cross-talk has occurred simply by looking at the colors, e.g., of the filter and/or media in the wells of the 384-well plate to determine if there is any deviation from a predetermined color pattern. FIG. 22 depicts one example of a predetermined color pattern for the 384-well plate assuming proper transfer of colored samples from four 96-well plates as described herein.

Note that the amount of colored solution employed is not critical, but in general should be between 2 µl to 30 µl, with 5 µl to 15 µl being preferred for the 96-well plates described. The colored solution can be added using various means, including a dropper, single pipette, multi-channel pipette, and automated means such as a multi-dropper machine marketed by Labsystems OY, of Helsinki, Finland. Further, although red, yellow, green and blue are preferred colors for both the alignment color coding and transfer color coding systems in accordance with.this invention, any variation of these colors may be used, and the intensity of color of each solution can be varied by using different amounts of colorant in the stock solutions. In addition, the sequence in which the samples are transferred from the differently dyed plates can be varied, but again, the sequence of red, yellow, green and blue may be preferred. As an alternative sequence, yellow, green, blue and red may be employed. Moreover, while it is more efficient to dye the filters of all wells in a plate, one could alternatively dye only filters of a selected well or wells which will actually be used.

The color-coded alignment technique and color-coded sample contamination detection technique described herein can be used independently or in combination. In a preferred embodiment, the color of the alignment means and the dyed filter of a 96-well plate will be the same. Further, the 96-well plate can be manufactured and marketed with the colorant pre-loaded on the filters of the 96-well filter plate and/or with the color-coded alignment guides already mounted on the plates. These plates could be available individually, or in pre-packaged kits. For example, a kit might comprise four 96-well plates, one each with a unique color-coded (e.g., red, yellow, green and blue) alignment guide, and optionally, filters pre-loaded with the corresponding colored dye. The kit optionally includes a 384-well plate having the corners color coded to match the coloring of the alignment means on the four 96-well plates.

In accordance with the present invention, various kits containing different multiwell plates to be stacked can be assembled. In most embodiments, these kits have at least two different types of multiwell plates which allow for direct transfer of material as described hereinabove.

For example, a kit for culturing and purifying a product or biological molecules of interest, such as a plasmid, can be provided wherein the kit comprises one to four 96-well filter plates for culture and subsequent clarification of lysed/potassium acetate precipitated product (such as a plasmid) and one or more 384-well plates having a porous retaining material, such as a filter or membrane, disposed in the bottom of each well. The kit would also include a gasket (such as gasket 30) affixed to the bottom of each 96-well plate or one or more rim gaskets for sealing the perimeter of the space between a 96-well plate and a 384-well plate when the 96-well plate is stacked thereon. Such kits may optionally include one or both of the (a) color-coded alignment guides, and (b) the color-coded contamination detection means previously described herein.

The 96/384 kits of the present invention further comprise reagents for culturing and purifying biological molecules, wherein the reagents can comprise a resuspension buffer, a lysis buffer, a potassium acetate ("KAc") precipitation buffer, and an elution buffer.

As a further example, a kit in accordance with the present invention would again comprise a kit for culturing and purifying a desired product or biological molecules of interest, such as a plasmid. This kit would include one 96-well filter plate for culturing and subsequent clarification of lysed/potassium acetate precipitated product, such as a plasmid, and one 96-well plate having a porous retaining material dispose in the bottom of each well. Each well of the second 96-well multiwell plate would be packed with a volume of size exclusion media on top of the porous retaining material and a volume of an absorptive media packed on top of the size exclusion media. A 96-well receiving plate is also included. Thus, use of this kit would involve transfer of material directly between 96-well plates.

The 96-well kits of the present invention may further comprise reagents for culturing and purifying biological molecules. The reagents could comprise a resuspension buffer, a lysis buffer, a potassium acetate ("KAc") precipitation buffer, a wash buffer, a desalting buffer or an elusion buffer.

The various reagents may be loaded into the wells of the 96-well or 384-well plates using a commercially available 96-well or 384-well pipettor, or by automated means such as a multi-dropper such as that sold by Labsystems OY of Helsinki, Finland. The 96-well pipettor may be used with either the 96-well or 384-well plates. In one embodiment of the present invention, the wells of a 384-well plate are prefilled with 100 µl of washing buffer (e.g., 0.5 M NaCl, 50 mM Tris), and this wash plate is placed above a 384-well plate containing the absorptive media, and the wash buffer is drawn through the absorptive media plate by a vacuum. Various other examples will be evident to those skilled in the art based upon the information provided herein.

To repeat, those skilled in the art will note from the above discussion that various techniques are provided herein for directly transferring samples from a first well plate having a first number of wells to a second well plate having a second number of wells, wherein the second number of wells may be greater than the first number of wells. Preferably, the second number of wells is a multiple of the first number of wells. As a specific example discussed herein, the first well plate may comprise a 96-well plate and the second well plate a 384-well plate. Significant time and processing complexity is saved by being able to directly transfer between two different multiwell plates. Pipetting apparatus is unnecessary to accomplish the transfer.

In addition to direct transfer of samples between well plates, a technique is provided herein to prevent cross-contamination between wells of the receiving plate, as well as to prevent drying of open wells within the receiving plate. In accordance with the principles of this invention, the first well plate may comprise a filter plate so that simultaneous transfer and filtering of samples occurs during the movement of samples from the first well plate to the second well plate. Further, the second well plate can comprise a chromatographic media so that purification of the sample can also simultaneously occur with transfer of the sample from the first well plate into and through the second well plate. Thus, in accordance with the principles of this invention, a greater volume of sample in the first well plate than can be accommodated in the second well plate can be simultaneously filtered in the first well plate, transferred from the first well plate to the second well plate and purified in the second well plate, before being discharged.

While the invention has been described in detail herein in accordance with certain preferred embodiments thereof, many modifications and changes therein may be effected by those skilled in the art. For example, those skilled in the art will understand that the concepts presented herein can be used in a multitude of combinations. Accordingly, it is intended by the appended claims to cover all such modifications and changes as fall within the true spirit and scope of the invention.

What is claimed is:

1. A device for processing biological/chemical samples comprising:

a first multiwell plate having x wells arranged in an array, each well of said x wells being capable of receiving a separate sample, and wherein each of said x wells has an outlet at a lower surface of the first multiwell plate;

a second multiwell plate having y wells arranged in an array, each well of said y wells being capable of receiving a separate sample, and wherein y>x and said outlets at the lower surface of said first multiwell plate are arranged to register with corresponding inlets of x' wells of said y wells of said second multiwell plate when said first multiwell plate is aligned with and stacked atop said second multiwell plate, wherein x'=x; and means for aligning said first multiwell plate to said second multiwell plate so that said x wells of said first multiwell plate automatically align to said x' wells of said second multiwell plate when said first multiwell plate is stacked atop said second multiwell plate using said means for aligning, whereby samples can be transferred from said x wells of said first multiwell plate to said x' wells of said second multiwell plate, wherein said means for aligning comprises first alignment indicia on said first multiwell plate at a first location and corresponding second alignment indicia on said second multiwell plate, wherein aligning of said first alignment indicia and said second alignment indicia when stacking said first multiwell plate atop said second multiwell plate facilitates said automatic aligning of said x wells of said first multiwell plate to said x' wells of said second multiwell plate, and wherein said first alignment indicia is adapted to be moved to a second location on said first multiwell plate so that a different set of x' wells of said second multiwell plate will be aligned with said x wells of said first multiwell plate.

2. The device of claim 1, wherein said first alignment indicia and said corresponding second alignment indicia comprise matching color indicia.

3. The device of claim 1, wherein y=(x×n) and n≧2, and wherein said device further comprises n first multiwell plates each having x wells arranged in an array, and each of said x wells being capable of receiving a separate sample, and wherein said means for aligning comprises n first alignment indicia on said n first multiwell plates, each first alignment indicia being disposed on a separate first multiwell plate, said means for aligning further comprising at least two second alignment indicia on said second multiwell plate, wherein at least two first alignment indicia on said first multiwell plates have corresponding second alignment indicia on said second multiwell plate.

4. The device of claim 3, wherein n=4, and wherein said means for aligning comprises four first alignment indicia one each on said four first multiwell plates, and four corresponding second alignment indicia on said second multiwell plate, each first alignment indicia having a corresponding second alignment indicia on said second multiwell plate, and wherein each first alignment indicia and corresponding second alignment indicia comprise matching color indicia.

5. The device of claim 4, wherein said x wells of said first multiwell plates comprise 96-wells and wherein said y wells of said second multiwell plate comprise 384-wells.

6. The device of claim 1, wherein said means for aligning further comprises an alignment guide coupled to either said first multiwell plate or said second multiwell plate so that said x wells of said first multiwell plate automatically align to said x' wells of said second multiwell plate when said first multiwell plate is stacked atop said second multiwell plate using said alignment guide.

7. The device of claim 6, wherein said alignment guide is coupled to said first multiwell plate and said first alignment indicia is disposed near said alignment guide.

8. The device of claim 7, wherein said first multiwell plate and said second multiwell plate have a common shape and similar size, and wherein said alignment guide is disposed at a corner of said first multiwell plate and extends downward therefrom for aligning thereof to a corner of said second multiwell plate, said corner of said second multiwell plate containing said corresponding second alignment indicia.

9. The device of claim 8, wherein said first multiwell plate and said second multiwell plate have a common rectangular shape, and wherein said x wells of said first multiwell plate comprise 96-wells, said y wells of said second multiwell plate comprise 384-wells, and said means for aligning comprises multiple second alignment indicia on said second multiwell plate, each second alignment indicia being disposed at a different corner of said second multiwell plate.

10. The device of claim 9, further comprising four first multiwell plates each having x wells arranged in an array, each well of said x wells being capable of receiving a separate sample, and wherein each well of said x wells has an outlet at a lower surface of the first multiwell plate, and wherein each multiwell plate of said four first multiwell plates has said common shape and similar size, and wherein said means for aligning comprises four alignment guides, each alignment guide being coupled to a different first multiwell plate so that said x wells of each first multiwell plate align to a different quadrant of said 384-wells of said second multiwell plate.

11. The device of claim 10, wherein said means for aligning further comprises four first alignment indicia on said four first multiwell plates, each first alignment indicia being disposed near the alignment guide coupled to a different first multiwell plate, and four second alignment indicia on said second multiwell plate, each first alignment indicia having a corresponding second alignment indicia on said second multiwell plate for facilitating aligning of each first multiwell plate to said second multiwell plate.

12. The device of claim 1, further comprising means for sealing said first multiwell plate to said second multiwell plate so that said first multiwell plate is stacked atop said second multiwell plate so that samples can be transferred from said x wells of said first multiwell plate to said x' wells of said second multiwell plate without cross-contamination occurring between wells of said second multiwell plate.

13. A device according to claim 1, wherein said first plate comprises a porous retaining material disposed over the outlet.

14. A device according to claim 13, wherein the porous retaining material is a filter.

15. A device according to claim 13, wherein said second plate comprises a porous retaining material disposed over an outlet.

16. A device according to claim 15, further comprising at least a first media disposed on the porous retaining material.

17. A device according to claim 16, wherein the media is an adsorptive media.

18. A device according to claim 16, wherein the media is a chromatography media.

19. A device according to claim 16, wherein the media is a size exclusion media.

20. A device according to claim 19, further comprising a second media disposed on the first media.

21. A device according to claim 20, wherein the second media is an absorptive media.

22. A device according to claim 20, wherein the second media is a chromatography media.

23. A device according to claim 22, wherein the chromatography media is an anion exchange media.

* * * * *